(12) United States Patent
Nomura et al.

(10) Patent No.: US 7,071,470 B2
(45) Date of Patent: Jul. 4, 2006

(54) MULTI-COMPONENT ANALYZING APPARATUS

(75) Inventors: Toshiyuki Nomura, Kyoto (JP); Hiroji Kohsaka, Kyoto (JP); Kennosuke Kojima, Kyoto (JP); Ichiro Asano, Kyoto (JP); Naoyuki Matsumoto, Kyoto (JP)

(73) Assignee: HORIBA, Ltd., Kyoto (JP)

( * ) Notice: Subject to any disclaimer, the term of this patent is extended or adjusted under 35 U.S.C. 154(b) by 179 days.

(21) Appl. No.: 10/659,436

(22) Filed: Sep. 11, 2003

(65) Prior Publication Data

US 2004/0149912 A1    Aug. 5, 2004

(30) Foreign Application Priority Data

Sep. 11, 2002 (JP) ............ P.2002-265436
Oct. 16, 2002 (JP) ............ P.2002-302263

(51) Int. Cl.
*G01N 21/35* (2006.01)
(52) U.S. Cl. .................... 250/339.13
(58) Field of Classification Search ......... 250/339.13
See application file for complete search history.

(56) References Cited

U.S. PATENT DOCUMENTS

| 3,832,548 | A |   | 8/1974 | Wallack |
| 4,772,789 | A |   | 9/1988 | Maram et al. |
| 4,891,518 | A |   | 1/1990 | Day |
| 5,294,796 | A |   | 3/1994 | Fee |
| 5,351,198 | A | * | 9/1994 | Adachi et al. ........ 702/24 |
| 5,498,873 | A |   | 3/1996 | Liebermann et al. |
| 5,508,525 | A |   | 4/1996 | Day et al. |

(Continued)

FOREIGN PATENT DOCUMENTS

JP    01073239 A  *  3/1989

(Continued)

OTHER PUBLICATIONS

Haaland, D. M. et al., "Application of New Least-Squares Methods for the Quantitative Infrared Analysis of Multicomponent Samples" Applied Spectroscopy, The Society for Applied Spectroscopy, Baltimore, US, vol. 36, No. 6, Nov. 1, 1982, pp. 665-673, XP000676150.

(Continued)

*Primary Examiner*—Constantine Hannaher
(74) *Attorney, Agent, or Firm*—Sughrue Mion, PLLC

(57) ABSTRACT

A multi-component analyzing apparatus in which infrared light is irradiated to a measuring-subject sample S which is constituted by either measuring-subject components whose sorts or quantities are limited or by a mixed article made of said measuring-subject components; intensity of infrared light having respective wavelength ranges which are fitted to infrared absorption spectra of the respective measuring-subject components among such infrared light penetrated through the measuring-subject sample S is measured by employing a plurality of detectors $4a$ to $4g$ corresponding thereto; and said multi-component analyzing apparatus is comprised of a calculation processing unit 6 for analyzing the infrared light intensity of the respective wavelength ranges so as to acquire concentration $x_1$ to $x_7$ of the respective measuring-subject components; wherein the calculation processing unit 6 is capable of executing an analyzing process program P for executing analysis operations of the concentration $x_1$ to $x_7$ of the respective measuring-subject components by solving simultaneous equations which are constituted by equations having mutual interference correction terms used to correct interference adverse influences occurred among the respective measuring-subject components.

11 Claims, 20 Drawing Sheets

U.S. PATENT DOCUMENTS

| | | | |
|---|---|---|---|
| 5,610,398 | A | 3/1997 | Anderson et al. |
| 5,750,994 | A | 5/1998 | Schlager |
| 6,341,257 | B1 | 1/2002 | Haaland |
| 2001/0045521 | A1 | 11/2001 | Prozzo et al. |
| 2003/0034445 | A1 | 2/2003 | Boyd et al. |
| 2003/0034454 | A1 | 2/2003 | Nomura et al. |

FOREIGN PATENT DOCUMENTS

| | | |
|---|---|---|
| JP | 2-124448 A | 5/1990 |
| JP | 10-510180 A | 10/1998 |
| JP | 11-510722 A | 9/1999 |
| JP | 2001-517791 A | 10/2001 |
| JP | 2002-5831 A | 1/2002 |
| WO | WO 96/17546 A1 | 6/1996 |
| WO | WO 97/47233 A1 | 12/1997 |
| WO | WO 99/15880 A1 | 4/1999 |
| WO | WO 00/55603 A1 | 9/2000 |

OTHER PUBLICATIONS

Bertran, E. et al., "Handling intrinsic non-linearity in near-infrared reflectance spectroscopy", Chemometrics and Intelligent Laboratory Systems, Elsevier Science Publishers B.V. Amsterdamn, NL, vol. 49, No. 2, Oct. 4, 1999, pp. 215-224, XP004255977.

Small, G. W., "Application of digital filtering and pattern recognition techniques to interferogram-based Fourier transform infrared qualitative analysis", Chemometrics and Intelligent Laboratory Systems, vol. 15, pp. 203-217, XP009027005 (1992).

* cited by examiner x2 TO x5 · · · CONCENTRATION x2 TO x5 ··· CONCENTRATION

MULTI-COMPONENT ANALYZING APPARATUS

BACKGROUND OF THE INVENTION

The present invention is related to a multi-component analyzing apparatus, particularly, to a mixed-refrigerant analyzing apparatus capable of analyzing refrigerant components contained in a mixed refrigerant in a separate manner.

Generally speaking, so-called "fluorocarbon" is conventionally used as refrigerants which are employed in refrigerating apparatus (cooling machines) such as, refrigerators and air conditioners. As to fluorocarbon, there is an HFC series of new refrigerants in addition to a CFC series and an HCFC series of old refrigerants. These series of fluorocarbon own various problems as to destruction of the ozone layer, and global warming trends in earth temperatures, so that there are duties to collect and recycling-use the above-described fluorocarbon. Also, such fluorocarbon which cannot be recycling-used must be firmly destroyed.

On the other hand, the fluorocarbon of R410A, R407C, R404A, and R507A which is typically known as the new refrigerants, corresponds to such mixed refrigerants which are formed by mixing several sorts of single-component fluorocarbon (R32, R125, R134a, R143a etc.) with each other in predetermined ratios. In addition, there is fluorocarbon R502 of the old refrigerant as the mixed refrigerant. On the other hand, in the case that a mixing ratio of collected fluorocarbon is not proper since fluorocarbon is collected in an erroneous manner, if this collected fluorocarbon is directly recycling-used, then there is a risk that performance of refrigerating apparatuss is deteriorated, or these refrigerating apparatuss are destroyed.

As a consequence, after fluorocarbon collecting industries have collected fluorocarbon, the collecting industries are required to confirm as to whether or not the collected fluorocarbon can be recycling-used by using such a fluorocarbon meter as described in Japanese Laid-open Patent Application No. Hei-2-124448, and then, are required to judge as to whether the collected fluorocarbon is recycle-used, or destroyed. In other words, concentration of fluorocarbon must be measured before, or after collections of the fluorocarbon in order to prevent erroneous collections and/or erroneous uses when the fluorocarbon is collected and recycling-used.

As means capable of measuring the above-described fluorocarbon concentration, the NDIR method has been proposed in, for example, the above-explained patent publication 1. In order to perform analysis of mixed refrigerants by using this NDIR method, such a mixed-refrigerant analyzing apparatus is employed. In this mixed-refrigerant analyzing apparatus, while an infrared light source is provided on one side of a cell to which a mixed refrigerant containing a plurality of refrigerant components is applied as sample gas, both a plurality of bandpass filters and a plurality of detectors are provided on the other side of this cell. The plural bandpass filters may pass therethrough infrared light (infrared rays) having wavelengths which are fitted to infrared absorption spectra of the above-explained refrigerant components-among infrared light which has passed through this cell. The plural detectors measure intensity of infrared light which has passed through these bandpass filters.

In this case, in order that a plurality of refrigerant components which constitute the mixed refrigerant may be individually detected in higher precision, infrared light transmission wavelength ranges of these bandpass filters which are provided in correspondence with the respective refrigerant components must be set in proper range conditions. In the conventional mixed-refrigerant analyzing apparatus, central wave numbers (namely, inverse numbers of wavelengths) of the above-explained bandpass filters have been determined by mainly considering such a wavelength band that infrared absorptions in the respective refrigerant components are large. For example, in the case that the single component fluorocarbon of R143a, R125, R134a, R32, R115, R12, and R22 is analyzed, as indicated in the below-mentioned table 1, the central wave numbers of the respective bandpass filters have been set.

TABLE 1

| | | | | | | unit: $cm^{-1}$ |
| | R143a | R125 | R134a | R32 | R115 | R12 | R22 |
|---|---|---|---|---|---|---|---|
| central wave number | 1235 | 1215 | 1187 | 1107 | 981 | 920 | 1117 |

However, in the above-described conventional mixed-refrigerant analyzing apparatus, as represented in the below-mentioned table 2, measurement errors of the respective refrigerant components are very large. More specifically, as to the fluorocarbon of R32 and R22, measurement error thereof are large.

TABLE 2

| R143a | R125 | R134a | R32 | R115 | R12 | R22 |
|---|---|---|---|---|---|---|
| less than 1% | 1.5% | less than 1% | 2.6% | less than 1% | 1.5% | 3.9% |

FIG. 19A and FIG. 19B indicate 100% absorbances of the fluorocarbon R32 and R22. As apparent from these graphic representations, such a fact can be revealed. That is, the absorbance of the fluorocarbon R32 is influenced by the fluorocarbon R22, and conversely, the absorbance of the fluorocarbon R22 is influenced by the fluorocarbon R32. In other words, these fluorocarbon R32 and R22 may have a so-called "mutual interference relationship" by which the fluorocarbon R32 and R22 may give interference influences to each other.

Also, FIG. 20 is a graphic diagram for representing both infrared absorption spectra of seven refrigerant components R143a, R125, R134a, R32, R115, R12, and R22, and also infrared transmission characteristics of the respective bandpass filters in a comparison manner. In this drawing, curves indicated by symbols "$A_1$" to "$A_7$" show the infrared absorption spectra of the above-described seven refrigerant components R143a, R125, R134a, R32, R115, R12, and R22, whereas curves denoted by symbols "$B_1$" to "$B_7$" represent the infrared transmission characteristics of the bandpass filters. As previously explained, in the conventional mixed-refrigerant analyzing apparatus, since the central wave numbers of the bandpass filters used to detect the respective refrigerant components have been set to the large infrared absorptions, namely have been set by mainly considering the low wavelength range of the infrared absorption spectra, the central wave numbers of the bandpass filters for the refrigerant components R32 and R22 have been set to such positions (values) where these central wave numbers are located in the vicinity of each other, as indicated in the curves "B$_4$" and "B$_7$" in FIG. 20. As a result, the measuring precision of these refrigerant components R32 and R22 is mutually deteriorated.

On the other hand, the Inventors of the present invention have filed U.S. patent application Ser. No. 10/207,783 (Publication 2003-0034454-A1) by which the simultaneous equations capable of correcting the mutual interference of the multiple components contained in the sample gas are solved so as to acquire the component ratios in such a similar case that a plurality of refrigerant components contained in a mixed refrigerant are analyzed. In such a calculation process operation is carried out, the following setting operation may constitute a very important aspect. That is, the infrared transmission wavelength ranges in the bandpass filters used to detect the refrigerant components corresponding to the measuring-subject components are set in such a manner that the desirable analysis results may be obtained.

In this measuring method, assuming now that a total number of measuring-subject components is "n", the intensity of the infrared light having the wavelength range fitted to the infrared absorption spectra of the respective measuring-subject components of the infrared light which has passed through the measuring-subject sample is measured by the non-dispersion type infrared gas analyzing meter (NDIR gas analyzing meter) having "n" pieces of the measuring devices. Then, in this non-dispersion type infrared gas analyzing meter, the absorbances "y$_1$" to "y$_n$" are calculated based upon the measurement values of the respective measuring devices, and then, the analyzing operation is carried out by employing the respective absorbances "y$_1$" to "y$_n$", so that the respective concentration "x$_1$" to "x$_n$" can be calculated.

It should be understood that since the above-explained absorbances "y$_1$" to "y$_n$" are defined as a logarithm of such a value obtained by subtracting measurement values of the respective detectors acquired when, for example, a measuring-subject sample is measured from measurement values acquired when zero gas is measured, attenuations of absorbances occurred by mixing the respective measuring-subject components with each other can be expressed by an addition, and thus, the subsequent calculation process operations can be carried out in a simple manner. As a result, since measurement values by the respective measuring devices may be sometimes obtained as logarithmically-calculated absorbances, it is so assumed that measurement values acquired by the respective measuring devices express the absorbances "y$_1$" to "y$_n$" in the below-mentioned descriptions. However, the present invention is not limited to this point.

The below-mentioned formula (1) corresponds to linear simultaneous equations which indicates one example of simultaneous equations employed so as to analyze the concentration "x$_1$" to "x$_n$", and represents a summation of one-dimensional equations corresponding to the concentration "x$_1$" to "x$_n$" of the respective measuring-subject components. In other words, since the linear simultaneous equations are solved, the respective concentration "x$_1$" to "x$_n$" can be analyzed based upon the measurement values "y$_1$" to "y$_n$" obtained by the respective measuring devices:

$$y_i = \sum_{j=1}^{n} (a_{ij} x_j) \quad \text{formula (1)}$$

It should be noted that the linear simultaneous equations are made of "n" pieces (i=1 to "n") of simultaneous equations. Symbol "i" shows a number of a detector, symbol "j" indicates a number of a measuring-object component, symbols "y$_1$" to "y$_n$" represent measurement values obtained from "n" pieces of the detectors which detect transmission light having different wavelength ranges from each other, symbols "x$_1$" to "x$_n$" show concentration as to "n" pieces of components, and symbol "a$_{ij}$" denotes a constant.

Also, in the simultaneous equations indicated in the above-explained formula (1), in such a case that there is no linear relationship between each of the component concentration "x$_1$" to "x$_n$" and a dependent variable (measurement values y$_1$ to y$_n$), and the respective component concentration x$_1$ to x$_n$ cannot be approximated to the dependent variable in a linear manner, as represented in a formula (2), such non-linear simultaneous equations with employment of a polynomial higher than, or equal to a quadratic equation may be employed:

$$y_i = \sum_{j=1}^{n} (a_{ij} x_j + b_{ij} x_j^2 + \cdots). \quad \text{formula (2)}$$

It should also be noted that symbols a$_{ij}$, b$_{ij}$, c$_{ij}$, . . . show constants, symbol "i" shows a number of a detector, and symbol "j" represents a number of a measuring-subject component.

However, since the above-described measurement values "y$_1$" to "y$_n$" acquired by the respective detectors are obtained in such a way that after such a infrared light having a predetermined wavelength range has been selectively penetrated by employing, for example, a plurality of optical filters among the infrared light which has passed through the measuring-subject sample, the respective detectors detect intensity of the infrared light which has passed through the respective optical filters, there is no way capable of avoiding such an event that several widths are produced in the wavelengths of the transmission light due to the filter characteristics of the optical filters. Then, the relationship between the filter characteristics of the optical filters and the infrared absorption spectra of the respective measuring-subject components may constitute an important element capable of establishing the relationship of the above-explained formulae (1) and (2).

However, as shown in FIG. 12, the infrared absorption spectra of the respective measuring-subject components own the wavelength dependent characteristics even in narrow ranges of the respective optical filters, and is overlapped with each other. As a result, such an adverse influence for distorting the filter characteristics of the above-explained optical filters is received by the infrared absorptions of other measuring-subject components mixed with each other, so that the absorbances which have been converted into the logarithms cannot become completely equal to such absorbances obtained by adding the absorbances to each other obtained by the respective measuring-subject components. Thus, there are some possibilities that errors caused by the interference influences may occur in the measurement values "y$_1$" to "y$_n$" detected by the respective detectors. It should be understood that in FIG. 12, symbols "Aa" to "Ag" represent infrared absorption spectra of the respective measuring-subject components, and symbols "Ba" to "Bg" show infrared transmittance characteristics of the optical filters.

FIG. 13 is a diagram for graphically indicating differences between calculation values of absorbances and measurement values of the absorbances, while these calculation values of absorbances obtained by substituting concentration of the respective measuring-subject components for the multi-dimensional (three-dimensional) simultaneous equations shown in the above-explained formula (2) when a mixing ratio of the fluorocarbon R125 and the fluorocarbon R134a as one example of the measuring-subject components is changed from 0% to 100%.

In FIG. 13, symbols "$C_{125}$" and "$C_{134a}$" represent calculation values of absorbances which are calculated every detector corresponding to each of the measuring-subject components by substituting concentration corresponding to a mixing ratio of the fluorocarbon R125 to the fluorocarbon R134a for the simultaneous equations. On the other hand, symbols "$D_{125}$" and "$D_{134a}$" indicate measurement values detected by the respective detectors when such a mixed gas of the fluorocarbon R125 and the fluorocarbon R134a is actually measured. As can be understood from FIG. 13, the largest differences between the calculation value $C_{125}$ and the measurement value $D_{125}$, and between the calculation value $C_{134a}$ and the measurement value D134a may appear when both the fluorocarbon R125 and the fluorocarbon R134a are mixed with each other in the ratio of 50 weight %. Also, a difference between the values $C_{125}$ and $D_{125}$ of the above-described absorbances is on the order of 0.008 at maximum, and is on the order of 2.7% with respect to the magnitude (0.30) of the absorbance.

In other words, as shown in the above-explained formula (2), in such a case that even when the quadratic equation, or higher polynomial is employed, there are mutually interference influences in the measured wavelengths of the respective components, there are some changes in outputs due to the component concentration which may cause the interference. Thus, even if the simultaneous equations as indicated in the formula (2) are solved, there are some possibilities that errors of several % happen to occur.

However, very recently, higher precision less than 1% is required for such multi-component analyzing apparatus capable of calculating concentration ratios of fluorocarbon, so that the conventional multi-component analyzing apparatus could not be suitably used in such higher precision.

Furthermore, specifically, in such multi-component analyzing apparatus, when a measurement is made of a standard sample constituted by single components, and also, another measurement is made of such a standard sample which is constituted by mixing a plurality of measuring-subject components with each other in predetermined concentration, higher precision may be required. Since a plurality of these measuring-subject components are mixed with each other in the preselected concentration, the measuring-subject components may mutually interfere with each other. As a result, there is no way to avoid such a fact that errors are increased.

SUMMARY OF THE INVENTION

The present invention has been made to solve the above-described problems, and therefore, has an object to provide a multi-component analyzing apparatus capable of improving calculation precision in each of component ratio calculations, for instance, with respect to a fluorocarbon concentration measuring apparatus which may measure component ratios of new/old mixed refrigerants (fluorocarbon) used in refrigerating/air conditioning machines.

Another object is to provide a mixed-refrigerant analyzing apparatus capable of analyzing a plurality of refrigerant components corresponding to measuring-subject components in high precision, while mutual interference of these plural refrigerant components may be suppressed as much as possible.

To achieve the above-described object, a multi-component analyzing apparatus, according to the present invention, is featured by such a multi-component analyzing apparatus in which infrared light is irradiated to a measuring-subject sample which is constituted by either measuring-subject components whose sorts or quantities are limited or by a mixed article made of the measuring-subject components; intensity of infrared light having respective wavelength ranges which are fitted to infrared absorption spectra of the respective measuring-subject components among such infrared light penetrated through the measuring-subject sample is measured by employing a plurality of detectors corresponding thereto; and the multi-component analyzing apparatus is comprised of a calculation processing unit for analyzing the infrared light intensity of the respective wavelength ranges so as to acquire concentration of the respective measuring-subject components; in which the calculation processing unit is capable of executing an analyzing process program for executing analysis operations of the concentration of the respective measuring-subject components by solving simultaneous equations which are constituted by equations having mutual interference correction terms used to correct interference adverse influences occurred among the respective measuring-subject components.

In the above-described analyzing process program, since the analyzing process operation is carried out by solving the simultaneous equations which are constituted by the equations having the mutual interference correction terms used to correct the interference adverse influences occurred among the respective measuring-subject components, even in such a case that the interference adverse influences are mutually given to each other in the measuring wavelength ranges of the respective measuring-subject component gas, the high-precision calculation can be carried out. Since the above-described mutual interference correction terms are employed in the analyzing calculation, the errors can be reduced to approximately 0.2 to 0.3 weight %, so that the precision of the analyzing calculation operation may be furthermore improved.

In addition, even when such interference adverse influences such as an overlapping phenomenon are given in the infrared absorption spectra of the respective measuring-subject components, the calculation processing unit analyzes the simultaneous equations having the mutual interference correction terms, the interference adverse influences can be firmly canceled. As a result, as to bandpass filters mounted on the respective detectors, the half-value widths thereof are no longer made unnecessarily narrow in order to avoid the partially overlapping effects of the infrared absorption spectra of the respective measuring-subject components. In other words, it is possible to provide such a low-cost multi-component analyzing apparatus whose performance does not depend upon the performance of the bandpass filters.

Also, sorts of measuring-subject components (namely, gas sorts) are not limited unless the infrared absorption spectra of the measuring-subject components are completely overlapped with each other over the entire range of the measurement wave numbers. In fact, with respect to any of measuring-subject samples constituted by mixing a plurality of measuring-subject components in which gas sorts and a total number of gas components to be handled have been previously limited, concentration ratios of these respective measuring-subject components may be calculated.

In the case that the mutual interference correction term includes a product made by multiplying a product of concentration of at least two measuring-subject components by one, or more mutual interference correction coefficients, since the simultaneous equations having the mutual interference correction term are solved, the mutual interference can be precisely corrected. This mutual interference correction term is made by multiplying a product of constants by the product of the concentration of at least two measuring-subject components.

As the simultaneous equations employed in the above-described analyzing calculation operation, for example, as indicated in the below-mentioned formula (3), such an idea may be conceived. That is, a product between concentration of a measuring-subject sample and a constant is multiplied plural times as a term which is added to a multi-dimensional (approximately three-dimensional) equation as a basic equation. It should be noted that the basic equation of the present invention is not limited only to the three-dimensional equation, but also not limited to such an equation to which a correction term is added:

$$y_i = \sum_{j=1}^{n} \left\{ (a_{ij}x_j + b_{ij}x_j^2 + c_{ij}x_j^3) \times \prod_{k=1}^{n} (1 + d_{ijk}x_k) \right\} \quad \text{formula (3)}$$

Note that in this formula (3), symbol "i" indicates a number of a detector, symbol "j" represents a number of a measuring-subject component, symbol "k" represents a number of a measuring-subject component which may interfere with a j-th measuring-subject component, symbol "n" shows a total number of measuring-subject components, and symbol "$d_{ijk}$" denotes a mutual interference correction coefficient, and when j=k, this mutual interference correction coefficient "$d_{ijk}$" is equal to zero.

It should be noted that the above-described invention indicates that the mutual interference correction term owns the product of the concentration of at least two measuring-subject components, but the present invention is not limited thereto. In other words, in such a case that the above-described mutual interference correction term is made by multiplying the product of the concentration of the two measuring-subject components by the mutual interference correction coefficient, the calculation processing unit can perform the analyzing operation in high precision by executing the analyzing calculation operation with employment of necessary minimum numbers of simultaneous equations, so that the calculation speed may be improved while sufficiently higher precision may be realized.

Also, since the mutual interference correction term is limited by such a product of the concentration of the two measuring-subject components, the above-described formula (3) may be simplified as indicated in, for example, the following formula (4):

$$y_i = \sum_{j=1}^{n} (a_{ij}x_j + b_{ij}x_j^2 + c_{ij}x_j^3) + \sum_{j=1}^{n} \sum_{k=j+1}^{n} d_{ijk}x_j x_k \quad \text{formula (4)}$$

In the case that the mutual interference correction coefficient is such a value obtained by dividing a difference by the product of the concentration of the two measuring-subject components, while the difference is calculated between a measurement value obtained by measuring a calibration-purpose sample formed by mixing two measuring-subject components with each other in a preselected ratio, and such a value obtained by substituting the concentration of the two measuring-subject components for such equations from which the mutual interference correction terms have been eliminated among the equations, the mutual correction coefficient may be easily calculated.

Also, in such a case that the equations are multi-dimensional equations; and the analyzing process program executes a stepwise calculation processing operation by which the concentration of the respective measuring-subject components is analyzed by employing simultaneous equations which are arranged by one-dimensional equations other than the multi-dimensional equations so as to calculate approximated values as to the concentration of the respective measuring-subject components, and the multi-dimensional simultaneous equations are converged by employing the approximated values, the calculation speed can be increased even when the analyzing operation is carried out in high precision.

In other words, the above-explained multiple stepwise calculating process operation implies that such a portion that the multi-dimensional equation of the present invention cannot be expressed by employing the one-dimensional equation may be compensated by the higher-order terms, while utilizing such a fact that the coefficient of the first-order term may become a large value capable of giving the highest influence. As a consequence, in such a case that the non-linear simultaneous equations are solved by using the Newton's method which is known as the numerical solving method of the equation, an approximated value is obtained from the one-dimensional equation, so that a solution may be converged in a very high speed.

In such a case that the above-explained calculation processing unit owns a standard sample correction coefficient which corresponds to either a ratio or a difference between measurement values of the respective detectors obtained by that while either standard samples made of single measuring-subject components or standard samples formed by mixing a plurality of measuring-subject components in predetermined concentration is employed, the respective standard samples are measured, and calculation values obtained by substituting the concentration of the standard samples for the simultaneous equations, and the standard sample correction coefficient has been stored in relation to each of the standard samples in order to further correct the simultaneous equations; and also the analyzing process program executes the analyzing process operation in the case that while the concentration of the respective measuring-subject components acquired by the analyzing process operation is compared with the concentration of the standard sample, when the relevant standard sample is present, the standard sample correction coefficient related to the relevant standard sample is employed so as to execute the analyzing process operation, if a one-point calibration is carried out in the vicinity of the concentration ratio of the standard sample, then such a precision lower than, or equal to 0.1 weight % may be expected.

According to the second aspect of the invention, a mixed-refrigerant analyzing apparatus employs the below-mentioned means.

In other words, a mixed-refrigerant analyzing apparatus, as recited in claim 1 of the present invention, is featured by such a mixed-refrigerant analyzing apparatus comprising: a cell to which a mixed refrigerant containing a plurality of refrigerant components is supplied as sample gas; an infrared light source for irradiating infrared light to the cell; a plurality of bandpass filters for penetrating therethrough infrared light having wavelengths which are fitted to infrared absorption spectra of the respective refrigerant components among infrared light which has penetrated the cell; and a plurality of detectors for measuring intensity of the infrared light which has penetrated the respective bandpass filters; in which at least two bandpass filters are provided among such bandpass filters, the infrared transmission central wave numbers of which are set to 1222 to 1235 cm$^{-1}$, 1205 to 1220 cm$^{-1}$, 1180 to 1192 cm$^{-1}$, 1065 to 1088 cm$^{-1}$, 981 to 1000 cm$^{-1}$, 908 to 933 cm$^{-1}$ and 798 to 820 cm$^{-1}$, respectively.

Also, a mixed-refrigerant analyzing apparatus of the present invention is featured by such a mixed-refrigerant analyzing apparatus comprising: a cell to which a mixed refrigerant containing a plurality of refrigerant components is supplied as sample gas; an infrared light source for irradiating infrared light to the cell; a plurality of bandpass filters for penetrating therethrough infrared light having wavelengths which are fitted to infrared absorption spectra of the respective refrigerant components among infrared light which has penetrated the cell; and a plurality of detectors for measuring intensity of the infrared light which has penetrated the respective bandpass filters; in which at least two bandpass filters are provided among such bandpass filters, the infrared transmission central wave-numbers of which are set to 1263 to 1269 cm$^{-1}$, 1137 to 1151 cm$^{-1}$, 1180 to 1192 cm$^{-1}$, 1065 to 1088 cm$^{-1}$, 981 to 1000 cm$^{-1}$, 908 to 933 cm$^{-1}$, and 798 to 820 cm$^{-1}$, respectively.

Also, a mixed-refrigerant analyzing apparatus of the present invention is featured by such a mixed-refrigerant analyzing apparatus comprising: a cell to which a mixed refrigerant containing a plurality of refrigerant components is supplied as sample gas; an infrared light source for irradiating infrared light to the cell; a plurality of bandpass filters for penetrating therethrough infrared light having wavelengths which are fitted to infrared absorption spectra of the respective refrigerant components among infrared light which has penetrated the cell; and a plurality of detectors for measuring intensity of the infrared light which has penetrated the respective bandpass filters; in which at least two bandpass filters are provided among such bandpass filters, the infrared transmission central wave numbers of which are set to 1222 to 1235 cm$^{-1}$, 1137 to 1151 cm$^{-1}$, 1180 to 1192 cm$^{-1}$, 1065 to 1088 cm$^{-1}$, 981 to 1000 cm$^{-1}$, 908 to 933 cm$^{-1}$, and 798 to 820 cm$^{-1}$, respectively.

Furthermore, a mixed-refrigerant analyzing apparatus of the present invention, is featured by such a mixed-refrigerant analyzing apparatus comprising: a cell to which a mixed refrigerant containing a plurality of refrigerant components is supplied as sample gas; an infrared light source for irradiating infrared light to the cell; a plurality of bandpass filters for penetrating therethrough infrared light having wavelengths which are fitted to infrared absorption spectra of the respective refrigerant components among infrared light which has penetrated the cell; and a plurality of detectors for measuring intensity of the infrared light which has penetrated the respective bandpass filters; in which at least two bandpass filters are provided among such bandpass filters, the infrared transmission central wave numbers of which are set to 1263 to 1269 cm$^{-1}$, 1205 to 1220 cm$^{-1}$, 1180 to 1192 cm$^{-1}$, 1065 to 1088 cm$^{-1}$, 981 to 1000 cm$^{-1}$, 908 to 933 cm$^1$ and 798 to 820 cm$^{-1}$, respectively.

In any of the above-described mixed-refrigerant analyzing apparatus with employment of the arrangements, since the infrared transmission wavelength ranges of the bandpass filters used to detect the respective plural refrigerant components are set based upon such a condition that the S/N is increased and interference influences caused by the own refrigerant component are not given to other refrigerant components, this mixed-refrigerant analyzing apparatus can analyze the respective refrigerant components of the mixed refrigerant in higher precision while suppressing the mutual interference caused by the plural refrigerant components as much as possible.

BRIEF DESCRIPTION OF DRAWINGS

FIG. 19A and FIG. 19B are diagrams for representing absorbances of the refrigerant components R32 and R22 when the conventional mixed-refrigerant analyzing apparatus is used; and FIG. 19C and FIG. 19D are diagrams for representing absorbances of the refrigerant components R32 and R22 when the mixed-refrigerant analyzing apparatus is employed.

DETAILED DESCRIPTION OF THE PREFERRED EMBODIMENTS

First Embodiment

Figure 1:
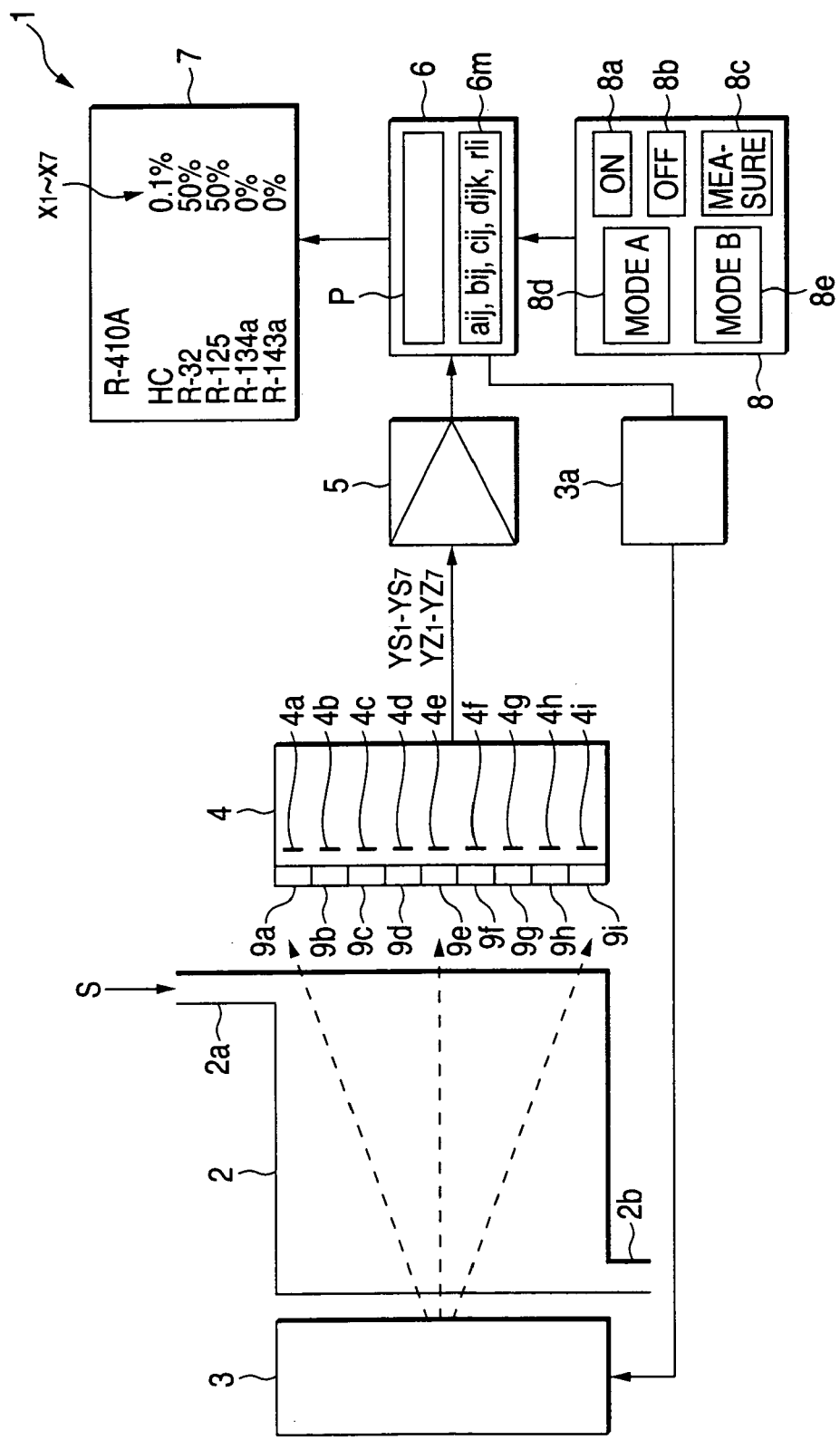
FIG. 1 is a diagram for indicating an entire arrangement of a multi-component analyzing apparatus of the present invention.

FIG. 1 is a schematic diagram for indicating an overall arrangement of a fluorocarbon concentration measuring apparatus functioning as an example of a multi-component analyzing apparatus according to the present invention. In FIG. 1, reference numeral 2 indicates a measuring cell used to conduct the fluorocarbon "S" which has been collected as one example of a measuring subject sample, and reference numeral 3 indicates an infrared light source for irradiating infrared light to the measuring cell 2. Also, reference numeral 4 indicates a detector for detecting transmission light of the infrared light, which has passed through the measuring cell 2. Reference numeral 5 shows an amplifier for amplifying a detection output from the detector 4. Reference numeral 6 represents a calculation processing unit which executes an analyzing process program "P" so as to perform an analyzing operation. In accordance with this analyzing process program P, intensity of transmission light amplified by the amplifier 5 is calculated/processed so as to acquire concentration (for example, weight %) the respective measuring-subject components. Reference numeral 7 shows a display unit for displaying thereon a measurement result, and reference numeral 8 indicates a keyboard used to enter operations by an operator.

On the keyboard 8, manual mode selecting buttons 8d and 8e are provided in addition to, for example, a power supply ON-button 8a, a power supply OFF-button 8b, and a measuring button 8c.

The measuring cell 2 of this example has, for instance, a flow inlet 2a of the fluorocarbon S and a flow outlet 2b of the fluorocarbon S. Then, in this fluorocarbon concentration measuring apparatus 1, the fluorocarbon S which has been collected into Bombe (not shown in this drawing) is acquired and conducted from the flow inlet 2a into the measuring cell 2. Under such a condition that the fluorocarbon S is filled into the measuring cell 2, concentration of this filled fluorocarbon S is measured.

It should be understood that while such a measuring-subject sample "S" whose concentration component is varied moment by moment is supplied to flow through the measuring cell 2, the multi-component analyzing apparatus 1 of the present invention may measure concentration components of this measuring-subject sample S in real time. In this alternative case, the multi-component analyzing apparatus 1 may be provided as a monitor within a fluid flowing path.

Also, while the multi-component analyzing apparatus 1 of the present invention is combined with a flow rate meter, a change contained in concentration of fluorocarbon which has been collected as the measuring-subject sample S is recorded and this recorded concentration change is integrated with a flow rate of this collected fluorocarbon, so that the multi-component analyzing apparatus 1 may measure a total amount of the collected fluorocarbon. Also, in the case that boiling points of respective single-component fluorocarbon which constitutes collected fluorocarbon are different from each other, even when the fluorocarbon is derived under vaporization state, a concentration ratio of fluorocarbon stored in Bombe may be correctly calculated.

Furthermore, since this example indicates such an example that the measuring-subject sample S is the fluorocarbon, the following description will be made as follows: That is, the multi-component analyzing apparatus is employed as a fluorocarbon concentration measuring apparatus 1, and the measuring-subject sample is employed as fluorocarbon "S". However, the present invention is not limited only to such a condition that the measuring-subject sample corresponds to the fluorocarbon S.

The above-described infrared light source 3 is, for example, a thin-film light source, and reference numeral 3a corresponds to a light source control unit of this thin-film light source 3. Then, while the light source control unit 3a supplies electric power to the thin-film light source 3 in an intermittent manner, the thin-film light source 3 irradiates infrared rays in the intermittent manner in connection with the supply of electric power from the light source control unit 3a, so that such a detector as a pyroelectric type detector may be employed. This pyroelectric type detector produces a signal which is directly proportional to a change of incident infrared rays. Also, the thin-film light source 3 can be made not only compact as well as can be operated in small power consumption, as compared with a general-purpose infrared light source, but also can emit the infrared rays in the interrupted manner in combination with the above-described light source control unit 3a. As a result, a chopper having a mechanical drive unit is no longer provided.

In other words, in the non-dispersion type infrared gas analyzing apparatus, since the above-described arrangement is employed, the infrared gas analyzing apparatus can be made compact, and the manufacturing cost thereof can be reduced. Further, warming-up operation of this infrared gas analyzing apparatus can be eliminated, so that easy operations thereof can be achieved, and also a content amount of the fluorocarbon S may be measured, while an operation may have a sense of a tester. In addition, since the mechanically operating member is omitted, the operation of this infrared gas analyzing apparatus can be carried out under stable condition, and also, occurrences of malfunction thereof can be suppressed.

The detector 4 contains 9 sorts of bandpass filters "9a" to "9i", and pyroelectric type detectors "4a" to "4i" which are employed in correspondence with the respective bandpass filters 9a to 9i. Since the pyroelectric type detectors 4a to 4i are employed as the detector in this embodiment mode, each of light receiving areas of these detectors can be made very small, for example, on the order of 0.1 to 1 mm$^2$, and a large number of these pyroelectric type detectors 4a to 4i and also a large number of these bandpass filters 9a to 9i can be provided in the array form. Seven sorts of bandpass filters 9a to 9g among the 9 sorts of bandpass filters 9a to 9i may limit wavelengths of infrared rays which may pass through these seven bandpass filters to a predetermined range in order to be fitted to infrared absorption spectra of 7 sorts of single components contained in the fluorocarbon S.

As apparent from the foregoing description, this does not imply that the respective single components contained in the collected fluorocarbon S are limited only to 7 sorts of single components in the multi-component analyzing apparatus 1 of the present invention. Even when how many single components of fluorocarbon are contained in the fluorocarbon S, a total number of bandpass filters 9a to 9i and also a total number of pyroelectric type detectors 4a to 4i may be set in accordance with a single component number of fluorocarbon S to be handled. The total number of these bandpass filters and pyroelectric type detectors are equal to at least a total number of single components contained in fluorocarbon S to be handled.

In this example, since the bandpass filters and the pyroelectric type detectors are employed as a reference purpose in order to correct light amount variations of the light source by employing such a wavelength range where infrared absorptions of the respective single components do not occur, and also are employed so as to measure concentration of lubricating oil mixed into refrigerants and also to perform the HC measurement for judging as to whether or not fluorocarbon can be recycling-used, the total number of these bandpass filters and of pyroelectric type detectors are selected to be larger than the total number of fluorocarbon components by 2.

In other words, the multi-component analyzing apparatus 1 of the present invention employs as the detector 4, plural sets of bandpass filters and pyroelectric type detectors, the total numbers of which are larger than, or equal to at least a total number of measuring gas sorts and of realizing reference purpose. It should be noted that since a total number of the measuring-subject components is seven sorts in this example, measurement values thereof may be represented as seven variables "$YZ_1$" to "$YZ_7$", "$YS_1$", and "$YS_7$".

Then, the above-described calculation processing unit 6 contains a storage unit "6 m". This storage unit 6m stores thereinto characteristics of the respective detectors 4a to 4i, characteristics of the respective bandpass filters 9a to 9i, and furthermore, respective coefficients (constants) "$a_{ij}$", "$b_{ij}$", "$c_{ij}$", "$d_{ijk}$", "$r_{1i}$", "$a'_{ij}$", and so on (will be explained later). Also, since the calculation processing unit 9 executes the analyzing process program P, this calculation processing unit 6 executes a calculation processing operation by employing the measurement values $YZ_1$ to $YZ_7$, $YS_1$ to $YS_7$, which are entered from the respective detectors 4a to 4g, and also, respective coefficients stored in the storage unit 6m in order to calculate concentration (weight %) of the fluorocarbon S every single component thereof.

The below-mentioned formula (5) shows such a formula capable of converting the above-described measurement values $YZ_1$ to $YZ_7$, $YS_1$ to $YS_7$ into absorbances "$Y_1$" to "$Y_7$". In other words, the absorbances "$y_1$" to "$y_7$" are assumed as logarithms of values obtained by subdividing the measurement values $YS_1$ to $YS_7$ to the measurement values $YZ_1$ to $YZ_7$, while the measurement values $YS_1$ to $YS_7$ are derived from the respective detectors 4a to 4g when the measuring-subject sample S is measured, and the measurement values $YZ_1$ to $YZ_7$ when the zero gas is measured:

$$y_i = -\log_{10}(YS_i/YZ_i) \quad \text{formula (5)}.$$

It should be noted that symbol "i" indicates a number of a detector, and i=1 to 7.

Referring now to the below-mentioned formula (6), simultaneous equations which are employed in analyzing process operation by way of the analyzing process program P will be explained. The simultaneous equations correspond to such equations to which a mutual interference correction term between two components is added, while this mutual interface correction term is obtained by multiplying a three-dimensional polynomial by a mutual interference correction coefficient "$d_{ijk}$". The three-dimensional polynomial passes through a zero point as an analytical curve segment of each of the measuring-subject components:

$$y_1 = f_1(x_1, x_2, \cdots, x_7) \quad \text{formula (6)}$$
$$= (a_{11}x_1 + b_{11}x_1^2 + c_{11}x_1^3) + \cdots + (a_{17}x_7 + b_{17}x_7^2 + c_{17}x_7^3) +$$
$$d_{112}x_1x_2 + d_{113}x_1x_3 + d_{114}x_1x_4 + \cdots + d_{117}x_1x_7 +$$
$$d_{123}x_2x_3 + d_{124}x_2x_4 + \cdots + d_{127}x_2x_7 \cdots +$$
$$d_{156}x_5x_6 + d_{157}x_5x_7 +$$
$$d_{167}x_6x_7$$

$$y_2 = f_2(x_1, x_2, \cdots, x_7)$$
$$= (a_{21}x_1 + b_{21}x_1^2 + c_{21}x_1^3) + \cdots + (a_{27}x_7 + b_{27}x_7^2 + c_{27}x_7^3) +$$
$$d_{212}x_1x_2 + d_{213}x_1x_3 + d_{214}x_1x_4 + \cdots + d_{217}x_1x_7 +$$
$$d_{223}x_2x_3 + d_{224}x_2x_4 + \cdots + d_{227}x_2x_7 \cdots +$$
$$d_{256}x_5x_6 + d_{257}x_5x_7 +$$
$$d_{267}x_6x_7$$

$$y_7 = f_7(x_1, x_2, \cdots, x_7)$$
$$= (a_{71}x_1 + b_{71}x_1^2 + c_{71}x_1^3) + \cdots + (a_{77}x_7 + b_{77}x_7^2 + c_{77}x_7^3) +$$
$$d_{712}x_1x_2 + d_{713}x_1x_3 + d_{714}x_1x_4 + \cdots + d_{717}x_1x_7 +$$
$$d_{723}x_2x_3 + d_{724}x_2x_4 + \cdots + d_{727}x_2x_7 \cdots +$$
$$d_{756}x_5x_6 + d_{757}x_5x_7 +$$
$$d_{767}x_6x_7$$

It should also be noted that the content of the above-explained formula (6) is such a content obtained by expanding a content of a summation "$\Sigma$" of the above-described formula (4); a term for multiplying the coefficients $a_{ij}$, $b_{ij}$, $c_{ij}$ corresponds to a portion which constitutes the conventional nonlinear simultaneous equations shown in the above-explained formula (2) in the multi-dimensional polynomial; and a term for multiplying the respective mutual interference correction coefficient "$d_{ijk}$" corresponds to the mutual interference correction term.

In the above-described formula (6), while the mutual interference correction coefficient "$d_{ijk}$" owns three affixes "i", "j", and "k", the affix "i" indicates the numbers of the detectors 4a to 4g; the affix "j" shows a number of a measuring-subject component which is mainly measured by each of the detectors 4a to 4g; and the affix "k" represents a number of such a refrigerant which may mutually interfere with a j-th measuring-subject component. Also, symbol "$f_i(x_1, x_2, \ldots, x_7)$" indicates a function provided with respect to each of the detectors 4a to 4g in order to calculate the absorbances $y_1$ to $y_7$ from the concentration $x_1, x_2, \ldots, x_7$ of the respective components. It is so assumed that any of these values "i", "j" "k" is defined as a value selected from 1 to 7.

The below-mentioned formula (7) corresponds to such a formula having standard sample correction coefficients "$r_{11}$" to "$r_{17}$" which are calculated every standard sample in order to obtain further correct values when a measurement is carried out as to the fluorocarbon R143a, R125, R134a, R22, R32, R115, R12 of the concentration 100 weight % as high-purity standard samples, and also another measurement is carried out with respect to mixed refrigerants of R404A, R407C, R407E, R410A, R507A, which are made by mixing a plurality of fluorocarbon with each other in defined concentration as standard samples:

$$y_i = r_{li} \times f_i(x_1, x_2, \ldots, x_7) \qquad \text{formula (7)}$$

It should be understood that symbol "i" is equal to 1 to 7. Also, symbol "l" shows the number of standard sample, and is equal to, for example, 12 sorts (l=1 to 12) of the above-explained single refrigerants (7 sorts) and the above-explained mixed refrigerants (5 sorts).

Furthermore, the following formula (8) corresponds to such a linear simultaneous equation which has been separatedly calculated in order to acquire an initial value of each of the concentration $x_1$ to $x_7$ when the non-linear simultaneous equations shown in the above-explained formula (6) are solved:

$$y_i = a'_{i1} x_1 + a'_{i2} x_2 + \ldots + a'_{i7} x_7 \qquad \text{formula (8)}$$

Note that symbol "i" is equal to 1 to 7.

The above-explained coefficients $a_{ij}$, $b_{ij}$ $c_{ij}$, $d_{ijk}$, $r_{li}$, $a'_{ij}$ etc. of the respective formulae (6) to (8) maybe determined by a calibration executed every multi-component analyzing apparatus 1 in order that these coefficients become such values fitted to, for instance, the characteristics of the respective units of each of the multi-component analyzing apparatus 1. This coefficient calibration is carried out by executing three calibration steps which are performed with respect to each of the multi-component analyzing apparatus 1, and then, the calibrated coefficients are stored in the storage unit 6m employed in the calculation processing unit 6.

Figure 2:
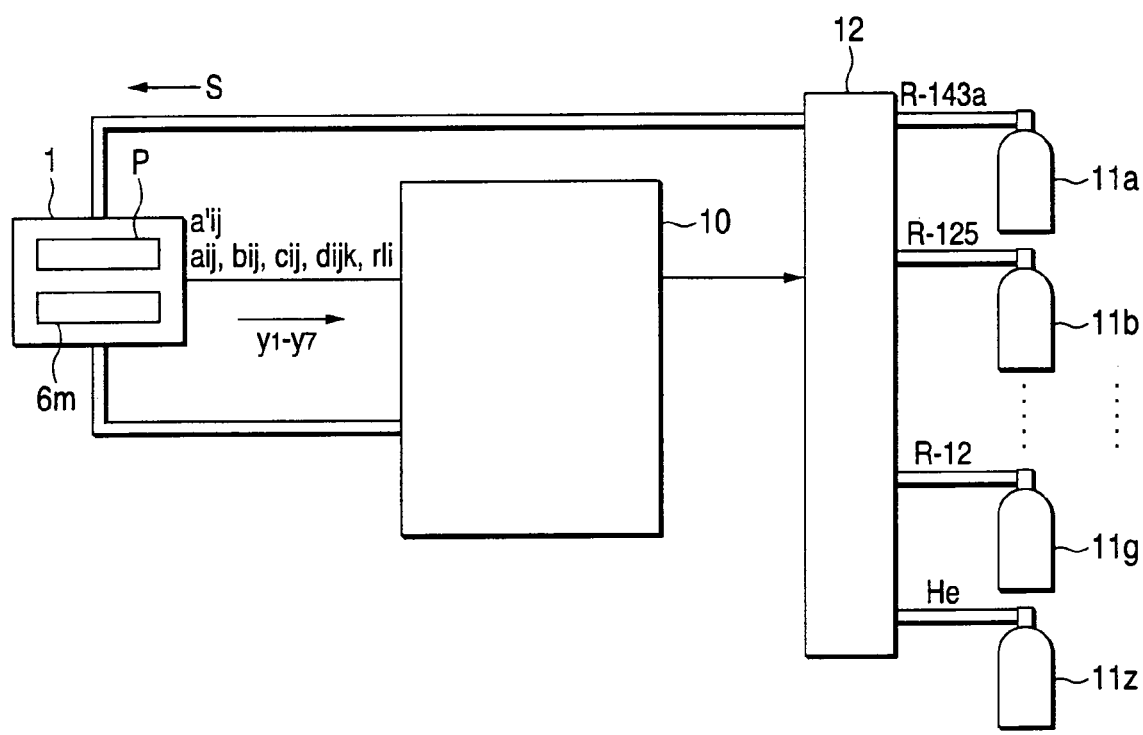
FIG. 2 is a diagram for showing an example of an inspection apparatus for calibrating the multi-component analyzing apparatus.
Figure 3:
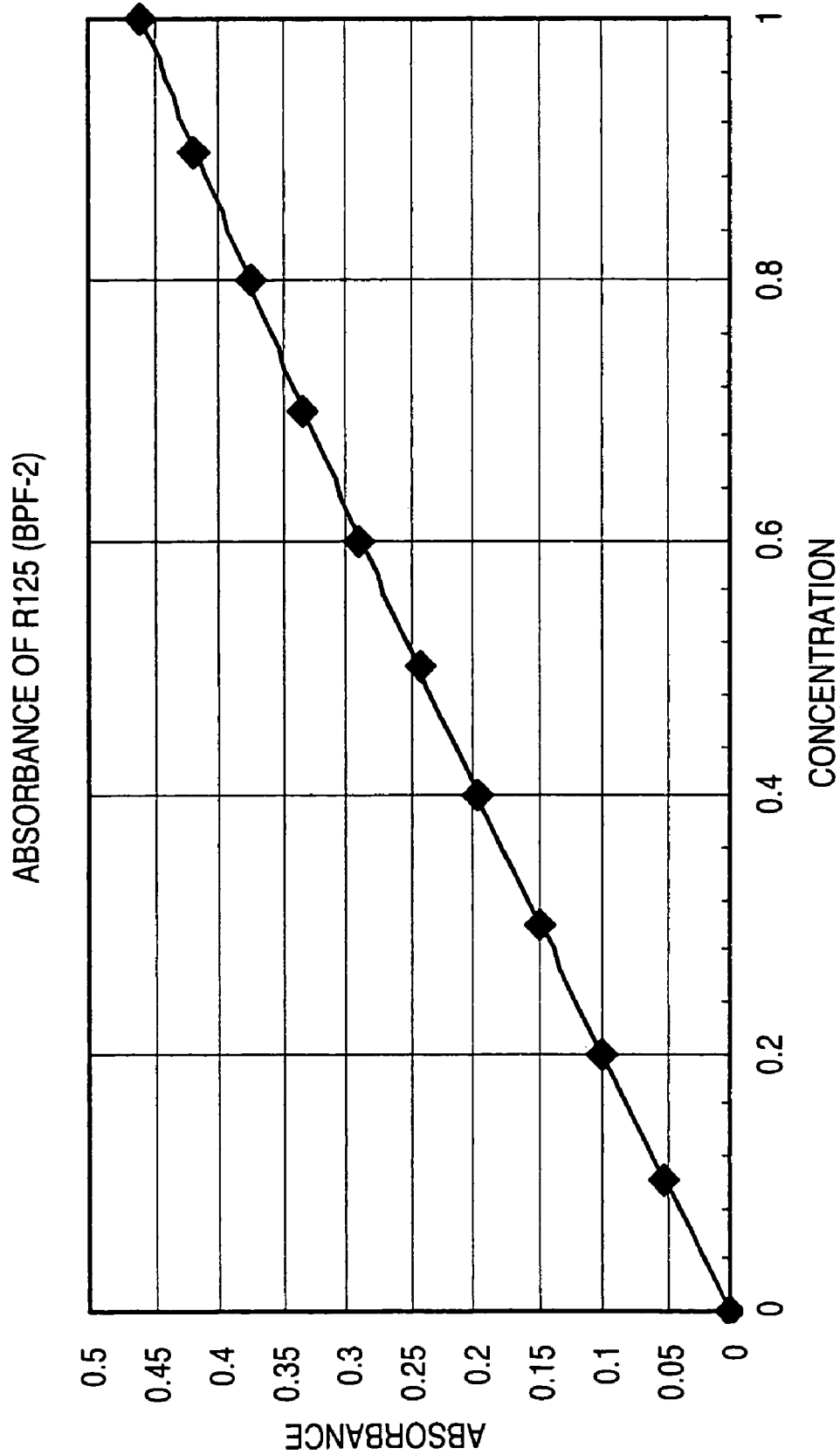
FIG. 3 is a diagram for showing a relationship between concentration of R125 and an absorbance detected by a second detector.
Figure 4:
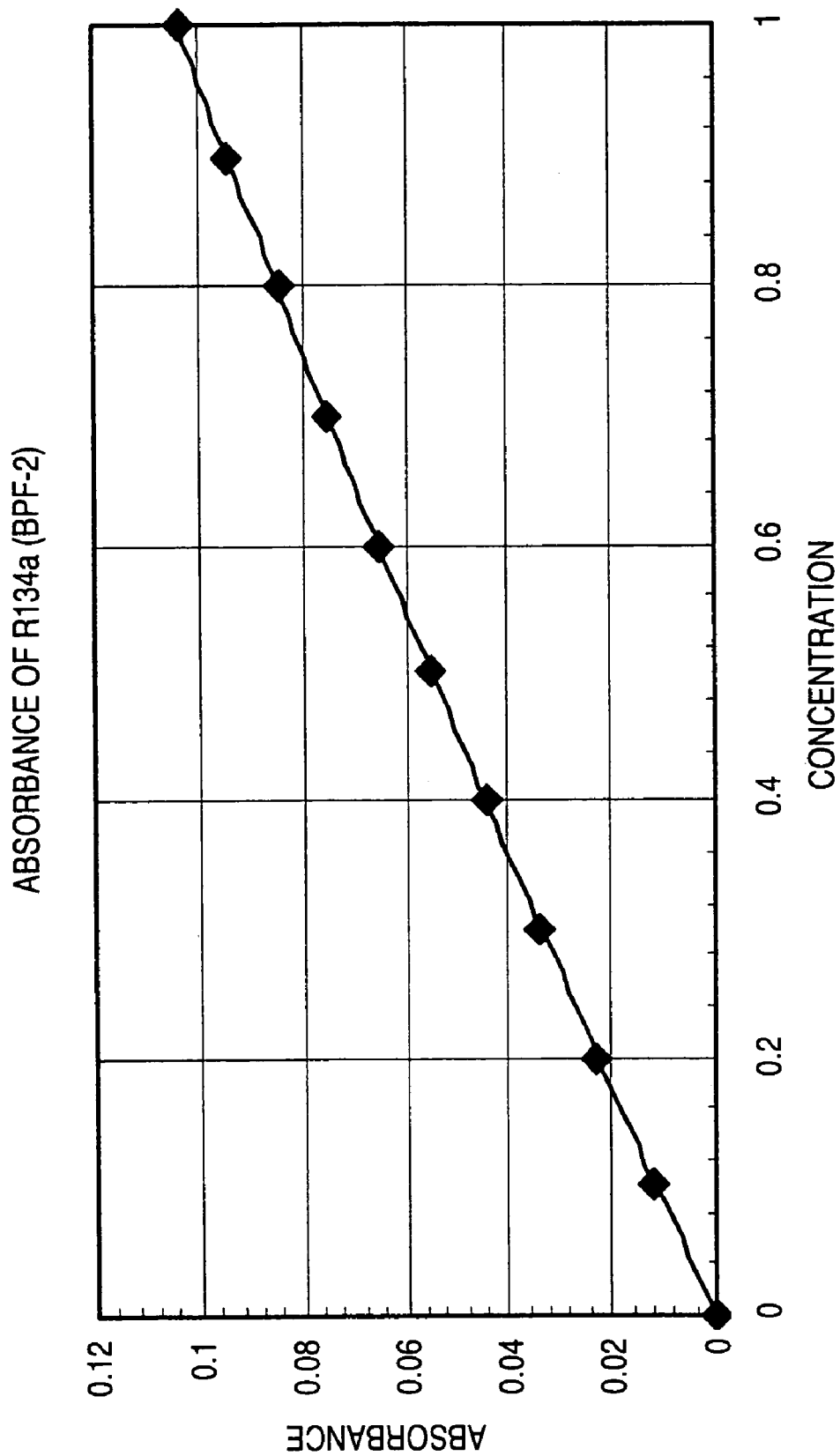
FIG. 4 is a diagram for indicating a relationship between concentration of R134a and an absorbance detected by the second detector.
Figure 5:
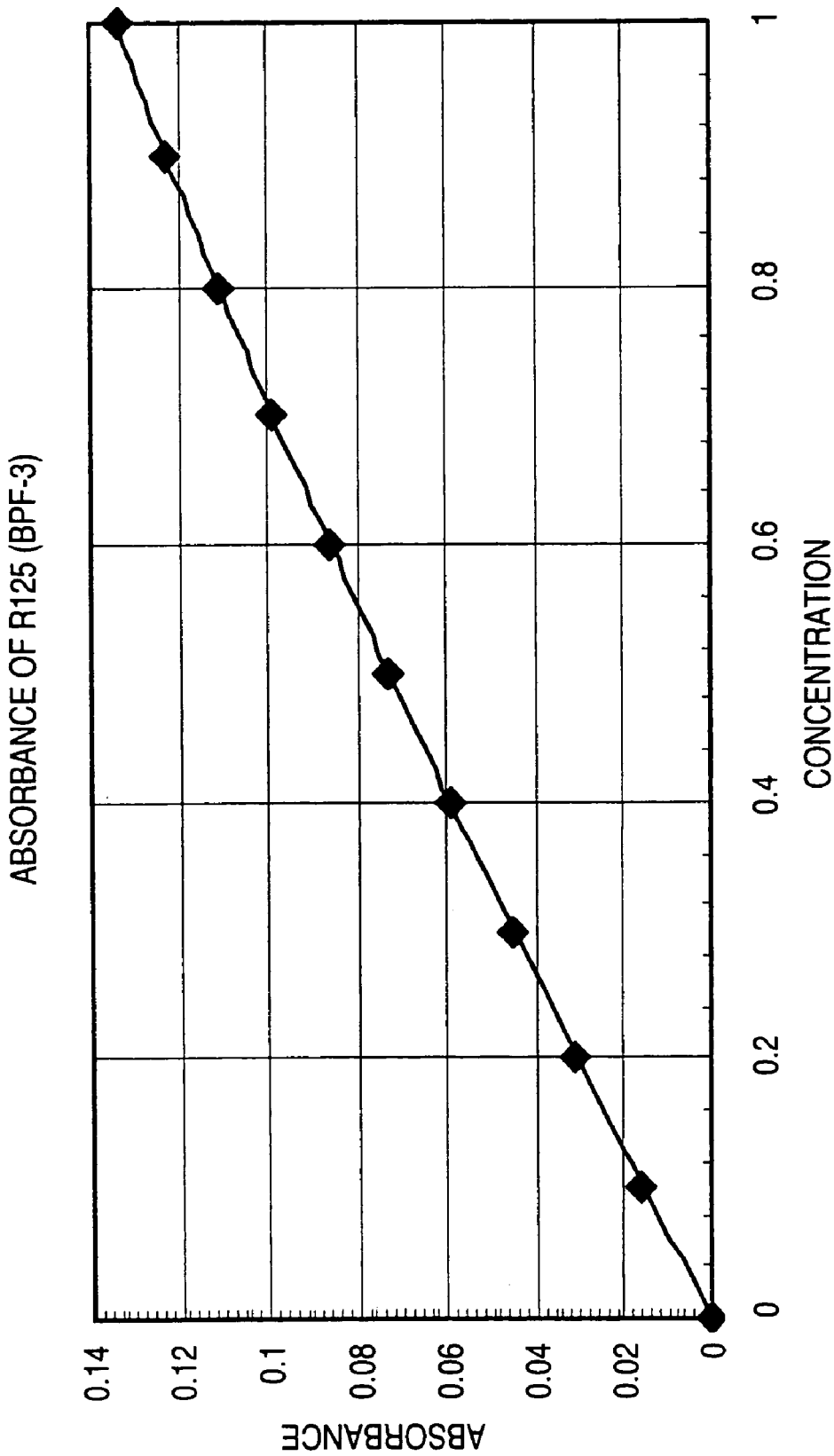
FIG. 5 is a diagram for showing a relationship between concentration of R125 and an absorbance detected by a third detector.
Figure 6:
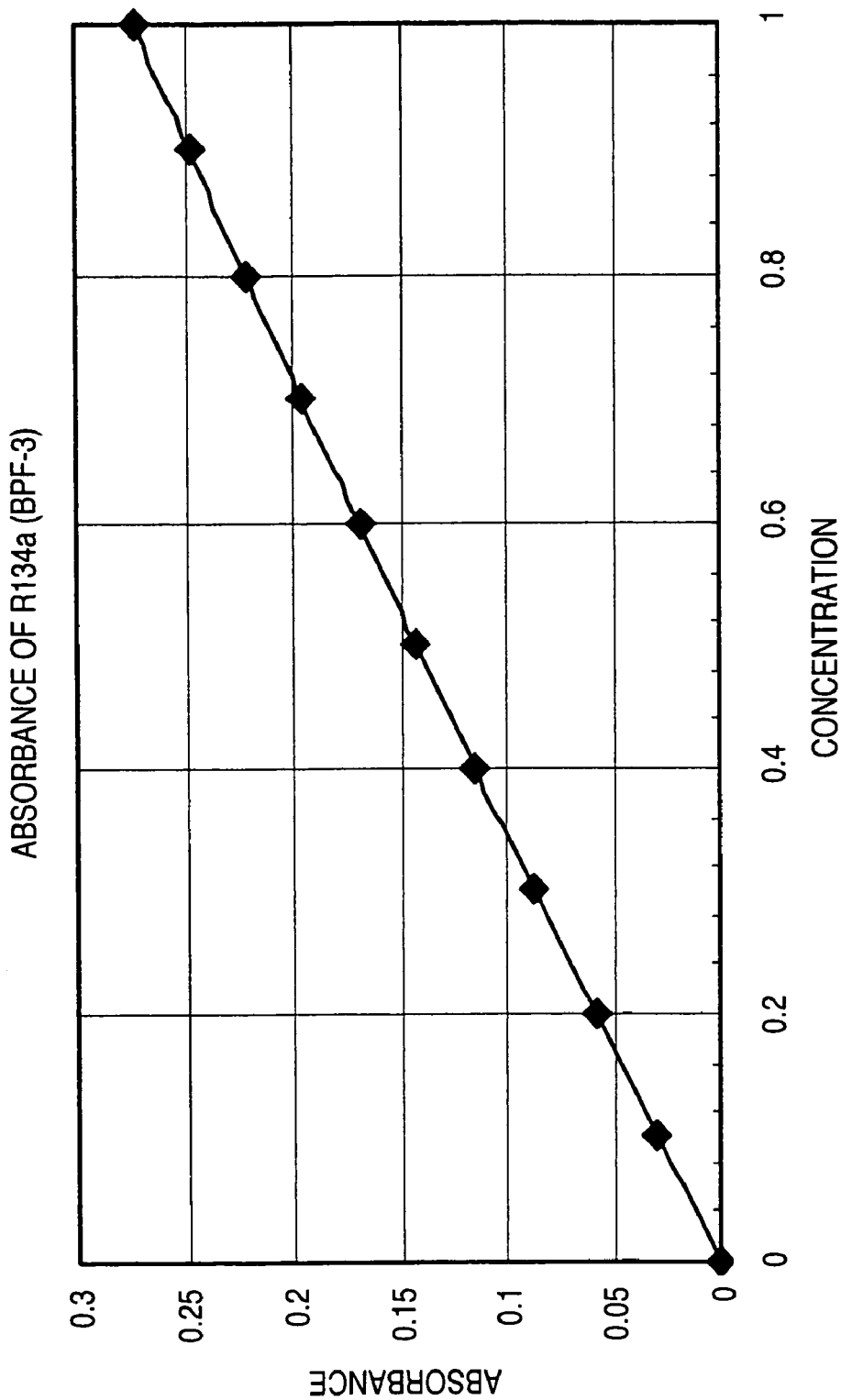
FIG. 6 is a diagram for indicating a relationship between concentration of R134a and an absorbance detected by the third detector.

FIG. 2 is an explanatory diagram for explaining a method of calibrating the above-explained multi-component analyzing apparatus 1. In FIG. 2, reference numeral 10 indicates an inspection apparatus of the multi-component analyzing apparatus 1. The inspection apparatus contains Bombe 11a to Bombe 11g used to fill, for example, single-component fluorocarbon of purity 100 weight %; Bombe 11z used to fill nitrogen gas as zero gas; and a dividing device 12 for selecting gas supplied from the respective Bombe 11a to 11g and 11z, or for mixing gas supplied from the respective Bombe 11a to 11g and 11z with each other in a proper ratio.

Then, the inspection apparatus 10 controls the dividing device 12 so as to supply proper gas to the multi-component analyzing apparatus 1, and also outputs measurement values (absorbances) $y_1$ to $y_7$ derived from the respective detectors when infrared light is caused to pass through the gas supplied to the multi-component analyzing apparatus 1 so as to obtain these measurement values. In other words, since the measurement values $y_1$ to $y_7$ are substituted for the above-described formulae (6) to (8), the inspection apparatus 10 may calculate the above-described coefficients $a_{ij}$, $b_{ij}$, $c_{ij}$, $d_{ijk}$, $r_{li}$, $a'_{ij}$ etc, which are specific to this multi-component analyzing apparatus 1.

It should also be understood that for the sake of simple explanations in this example, one set of the multi-component analyzing apparatus 1 is connected to the inspection apparatus 10 so as to calibrate this single set of multi-component analyzing apparatus 1. In an actual case, while a plurality of multi-component analyzing apparatus are connectable to this inspection apparatus 10, it is preferable that a plurality of multi-component analyzing apparatus 1 may be calculated by the inspection apparatus 10 at the same time.

The multi-dimensional polynomial of this example is the three-dimensional polynomial having the three coefficients of $a_{ij}$, $b_{ij}$, $c_{ij}$. As a consequence, three-dimensional basic analytical curves must be acquired every 7 sorts of fluorocarbon. Thus, first of all, as a first step of the calibration operation, for example, while the nitrogen gas is employed as the base, a single component of fluorocarbon S which has been mixed in each concentration of 20 weight %, 40 weight %, 60 weight %, 80 weight %, and 100 weight % is supplied to the multi-component analyzing apparatus 1. Then, when the respective single-component fluorocarbon S is measured, the inspection apparatus 10 of this example calculates the absorbances "$y_1$" to "$y_7$".

In this case, the coefficients $a_{ij}$, $b_{ij}$, $c_{ij}$ contained in the formula (6) maybe calculated by employing the least squares method from, for example, measurement values at 6 points involving the concentration 0%. In other words, since the 7 sorts of refrigerants are measured at 5 points, the coefficients $a_{ij}$, $b_{ij}$, $c_{ij}$, specific to this multi-component analyzing apparatus 1 may be specified (calibrated).

FIG. 3 to FIG. 6 are diagrams for indicating relationships between the absorbances "$y_2$" and "$y_3$" which are measured by the detectors 4b and 4c via the bandpass filters 9b and 9c, and the concentration "$x_2$" and "$x_3$" of the fluorocarbon R125 and R134a as one example.

It should also be noted that since the analytical curve constituting the base is expressed by the three-dimensional equation in this example, the three coefficients $a_{ij}$, $b_{ij}$ $c_{ij}$ must be acquired, and thus, the respective coefficients are obtained by performing the least squares method of the six points involving the origin. However, according to the present invention, the degree of the analytical curve constituting the base is not limited only to the three-dimensional equation. In other words, in order to execute a measuring operation in higher precision, while an order of an analytical curve may be increased, concentration is changed in more precise steps, so that the respective coefficients $a_{ij}$, $b_{ij}$, . . . may be obtained. Conversely, in the case that the analytical curve constituting the base may be approximated by a two-dimensional analytical curve, the concentration is changed in larger steps so as to obtain the coefficients $a_{ij}$, $b_{ij}$, so that time required for the calibration operation may be shortened.

Also, the coefficient $a'_{ij}$ contained in the above-described formula (8) may also be obtained at the same time. As indicated in FIG. 3 to FIG. 6, although the relationships between the absorbances and the concentration are more or less curved in this example, since the relationships are changed in substantially linear manners, this coefficient $a'_{ij}$ may become nearly equal to the value of the coefficient $a_{ij}$. It should be noted that these coefficients $a'_{ij}$, $a_{ij}$, $b_{ij}$, . . . , are stored in the storage unit 6m of the multi-component analyzing apparatus 1.

Next, as a second step of the calibration operation, two sorts of fluorocarbon selected from seven sorts of single fluorocarbon are mixed with each other in such a manner that a weight ratio of the fluorocarbon may become, for example, 40:60, and then, measurement values "$y_1$" to "$y_7$" are obtained under such a condition that this mixed fluorocarbon is supplied to the multi-component analyzing apparatus 1. Then, as represented in the following formula (9), a calculation is made of a difference between each of these measurement values "$y_1$" to "$y_7$" and a logic value obtained from the above-explained basic analytical curve, and this difference is divided by a product of concentration of the respective fluorocarbon, so that the above-explained mutual interference correction coefficient "$d_{ijk}$" is obtained. That is to say, the logic value corresponds to such a value obtained by substituting the concentration of the above-described two measuring-subject components for such an equation defined by eliminating the mutual interference correction term from the equations indicated in the formula (6):

$$d_{ijk}=(y_{ijk}-(a_{ij}*s_j+b_{ij}*s_j^2+c_{ij}*s_j^3)-(a_{ik}*s_k+b_{ik}*s_k^2+c_{ik}*s_k^3))/(s_j*s_k) \quad \text{formula (9)}$$

It should be noted that symbol "$y_{ijk}$" denotes an output (after being converted into absorbance) from an i-th detector when single-component fluorocarbon "j" is mixed with single-component fluorocarbon "k" in a ratio of $s_j$:$s_k$. Symbols "$s_j$" and "$s_k$" represent concentration of the fluorocarbon "j" and "k".

As to this mutual interference correction coefficient "$d_{ijk}$", the calibration operation may be carried out plural times which are equal to, for example, a total combination number of 7 sorts of fluorocarbon. For instance, since the calibration operation is carried out 21 times, all of the mutual interference correction coefficients $d_{ijk}$ may be obtained. Then, the mutual interference correction coefficients disk are stored in the storage unit 6m.

Next, as a third step of the calibration operations, while standard fluorocarbon is employed which is constituted by 7 sorts of single-component fluorocarbon of 100 weight % and mixed-component fluorocarbon (5 sorts of R404A, R407C, R407E, R410A, and R507A), the coefficient "$r_{li}$" (standard sample correction coefficient) of the above-explained formula (7) is calculated. A table 1 represents a relationship of weight % between the above-explained fluorocarbon of the mixed components as one example of the standard sample, and each of the measuring-subject component (single fluorocarbon):

TABLE 3

|  | R404A | R407C | R407E | R410A | R507A |
|---|---|---|---|---|---|
| R32 | — | 23.0 | 25.0 | 50.0 | — |
| R125 | 44.0 | 25.0 | 15.0 | 50.0 | 50.0 |
| R134a | 4.0 | 52.0 | 60.0 | — | — |
| R143a | 52.0 | — | — | — | 50.0 |

Under such a condition that the above-explained respective fluorocarbon is supplied to the multi-component analyzing apparatus 1, measurement values "$y_1$" to "$y_7$" are obtained. Then, as shown in the below-mentioned formula (10), while such values obtained by substituting predetermined concentration of each of the fluorocarbon for the multi-dimensional equation $f_i$ ($x_1$, $x_2$, ..., $x_7$) indicated in the above-described formula (6), a ratio of this value to each of the measurement values "$y_1$" to "$y_7$" is calculated as the standard sample correction coefficient "$r_{li}$":

$$r_{li}=y_i/f_i(x_1, x_2, \ldots, x_7) \quad \text{formula (10)}$$

Note that symbol "l" is equal to 1 to 12, and symbol "i" is equal to 1 to 7.

Subsequently, the calculated standard sample correction coefficiency $r_{li}$ is stored into the storage unit 6m. The standard sample correction coefficient "$r_{li}$" calculated in this case is substantially equal to 1, and may finally correct such a very small error which could not be corrected by the above-explained mutual interference correction term, and further, this standard sample correction coefficient $r_{li}$ corresponds to such a correction coefficient which may become effective in order to measure defined fluorocarbon whose mixing ratio is determined in higher precision.

This example indicates that in the above-explained formula (10), the ratio of the measurement values "$y_1$" to "$y_7$" to the multi-dimensional equation $f_i$ ($x_1$, $x_2$, ..., $x_7$) is used as the standard sample correction coefficient $r_{li}$. However, the present invention is not limited only to this point. In other words, as shown in the below-mentioned formula (11), a difference between the measurement values "$y_1$" to "$y_7$" and the multi-dimensional equation $f_i$ ($x_1$, $x_2$, ..., $x_7$) may be used as a standard sample correction coefficient "$m_{li}$" becomes substantially equal to zero:

$$m_{li}=y_i-f_i(x_1, x_2, \ldots, x_7) \quad \text{formula (11)}$$

Note that symbol "l" is equal to 1 to 12, and symbol "i" is equal to 1 to 7.

Alternatively, a correction using the standard sample correction coefficient "$m_{li}$" may be carried out in accordance with the below-mentioned formula (12)

$$y_i=f_i(x_1, x_2, \ldots, x_7)+m_{li} \quad \text{formula (12)}$$

Note that symbol "l" is equal to 1 to 12, and symbol "i" is equal to 1 to 7.

Furthermore, in this example, while the above-described formula (4) is employed as the base, since the calculation is carried out by mainly using the formula (6) obtained by expanding the formula (4), the method for calculating the respective coefficients $a_{ij}$, $b_{ij}$, $c_{ij}$, $d_{ijk}$, $r_{li}$ (or $m_{li}$), and $a'_{ij}$ has been explained as the above-explained method. However, the present invention is not limited only to this method. In other words, in such a case that while the above-explained formula (3) is employed as the base, such a formula obtained by expanding this formula (3) is employed, although contents of coefficients are different from the above-explained coefficients, there is no large difference between the calculation methods of both cases.

Since the above-explained calibration is carried out, all of the coefficients required to perform the correct measuring operations for the multi-component analyzing apparatus 1 can be obtained. In other words, while the multi-component analyzing apparatus 1 is separated from the inspection apparatus 10, unknown measuring-subject sample "S" can be measured.

Figure 7:
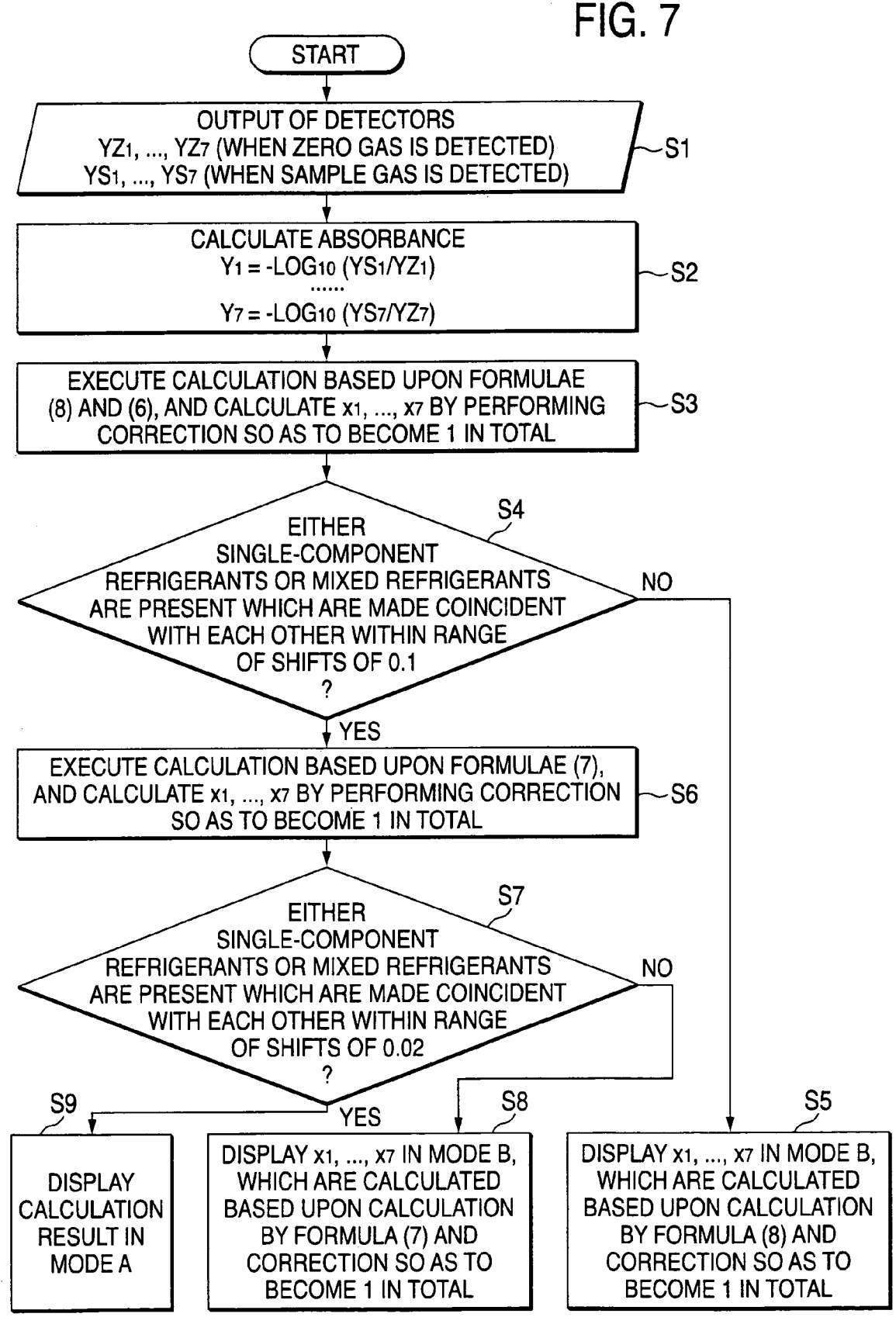
FIG. 7 is a diagram for indicating an example of operations of an analyzing process program.

FIG. 7 is a flow chart for describing an example of process operations of the analyzing process program P executed by the above-described calculation processing unit 6. In FIG. 7, a step "S1" indicates a step for inputting outputs $YZ_1$ to $YZ_7$, $YS_1$ to $YS_7$ of the respective detectors. It should be understood that symbols $YZ_1$ to $YZ_7$ show outputs from the respective detectors 4a to 4g when the zero gas is measured, symbols $YS_1$ to $YS_7$ denote outputs from the respective detectors 4a to 4g when the measuring-subject sample S is measured.

A step "S2" is a step for calculating absorbances based upon the respective outputs $YZ_1$ to $YZ_7$, $YS_1$ to $YS_7$. In this step S2, the logarithmic calculation indicated in the above-explained formula (5) is carried out, so that the respective absorbances $y_1$ to $y_7$ can be calculated.

A step "S3" corresponds to a step in which concentration $x_1$ to $x_7$ of the respective measuring-subject components is calculated by executing the calculation operations defined in the above-explained formulae (8) and (6). In other words, in this step S3, approximated values as to the concentration $x_1$ to $x_7$ are firstly calculated by employing the formula (8) constructed of the linear equation, and thereafter, the non-linear simultaneous equations defined in the above-explained formula (8) are analyzed in accordance with the Newton's method by employing the approximated values of the concentration $x_1$ to $x_7$. Then, the values of the concentration $x_1$ to $x_7$ are corrected by way of a proportional calculation in such a manner that a total value of the calculated concentration $x_1$ to $x_7$ becomes equal to "1". It should be noted that since a minus value among the concentration $x_1$ to $x_7$ is mainly caused by noise and the like, the detection levels of which are lower than, or equal to detection limit values, this minus value is calculated as "0".

In other words, since a stepwise calculating operation is carried out with respect to the calculations of the concentrations $x_1$ to $x_7$ instead of such a calculating operation that the concentration $x_1$ to $x_7$ is calculated by using the multi-dimensional simultaneous equations defined by the above-explained formula (8) from the beginning step, the analyzing process operation using the Newton's method and the like may be carried out in a high speed. That is, in this stepwise calculating process operations, the simultaneous equations of the formula (6) constructed of the one-dimensional equations are firstly employed so as to perform analyzing operation, so that the approximated values of the concentration as to the respective measuring-subject components are obtained. Then, such an analyzing calculation capable of converging the above-explained multi-dimensional simultaneous equations is carried out by employing these approximated values.

A step "S4" corresponds to such a step for judging as to whether or not a standard sample made of single components, or mixed components is present. In this standard sample, the respective component ratios of the concentration $x_1$ to $x_7$ of the respective measuring-subject components which have been acquired by the analyzing operation of the above-described formula (8) are made coincident with each other within the range of shifts of 0.1. In this step S4, when such a judgement is made that the relevant standard sample is not present, the process operation jumps to another step S5.

Figure 8:
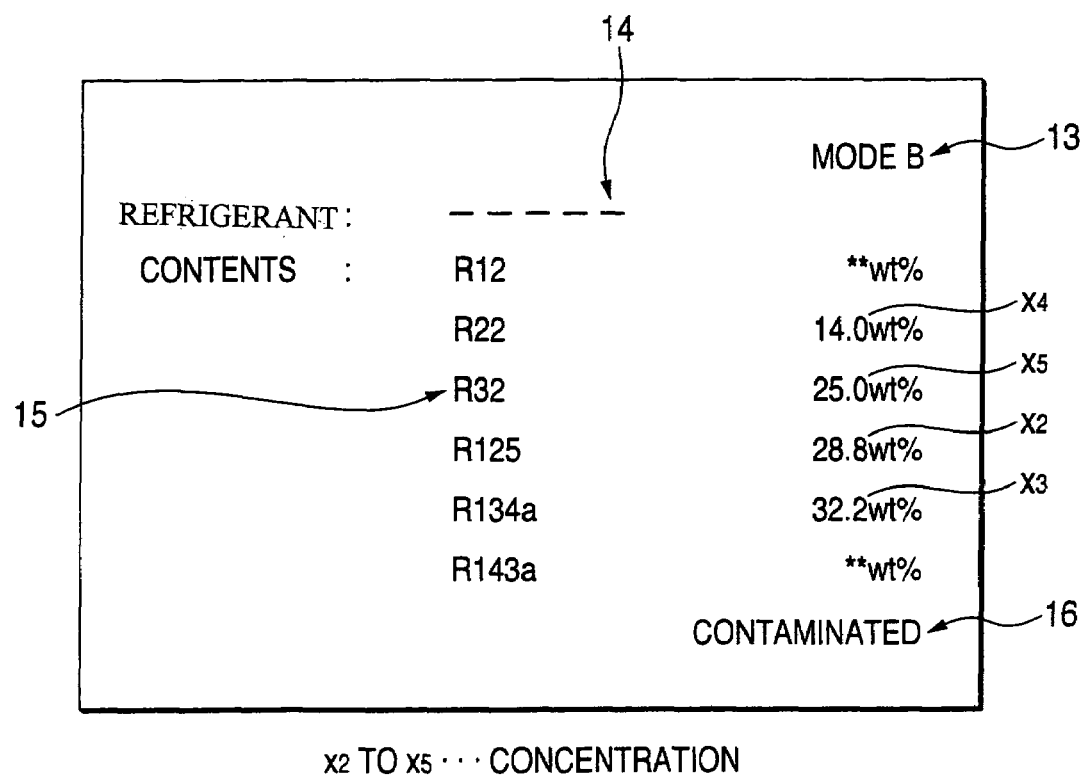
FIG. 8 is a diagram for indicating a display example of an analysis result.

That is to say, this step "S5" corresponds to such a step for directly displaying on the display unit 7, the respective component concentration $x_1$ to $x_7$ of the mixed fluorocarbon which does not correspond to the standard sample. FIG. 8 is a diagram for indicating a display example in the case that the relevant standard sample is not present. In FIG. 8, reference numeral 13 shows a calculation mode display unit, reference numeral 14 indicates a display portion of the relevant refrigerant, reference numeral 15 represents a display portion indicative of concentration of the respective refrigerants, and reference numeral 16 shows a display portion of a message supplied from the multi-component analyzing apparatus 1.

In the case shown in FIG. 8, the mode display portion 13 displays a display result obtained by the B mode. Also, since there is no relevant refrigerant, such a symbol "- - - " is displayed on the display portion 14, and none of relevant fluorocarbon name is displayed. Also, the display portion 15 displays thereon weight % of the respective fluorocarbon containing amounts larger than, or equal to a predetermined amount. It should be noted that symbol "**" shows a component lower than, or equal to a detection limit. In addition, a display content "CONTAMINATED" of the message display portion 16 indicates such a message that the measuring-subject sample S is contaminated by other components.

A step "S6" corresponds to a step which is executed when it is so judged in the previous step S4 that there is such a standard sample whose component ratios are made coincident with each other with the range of the shift of 0.1. In this step, the above-explained standard sample correction coefficient $r_h$ maybe selected from the number 1 of the selected standard sample, and concentration $x_1$ to $x_7$ of the respective components is again calculated by executing the calculation defined in the above-explained formula (7). Then, the values of the concentration $x_1$ to $x_7$ are corrected by executing the proportional calculation in such a manner that a total value of the calculated concentration $x_1$ to $x_7$ becomes equal to 1. Also, a minus value of the concentration $x_1$ to $x_7$ is calculated as "0".

A step "S7" corresponds to such a step for judging as to whether or not such a standard sample made of either the single components or the mixed components is present in which the respective component ratios of the calculated concentration $x_1$ to $x_7$ are made coincident with each other within the range of the shifts of 0.02. In this step, when it is so judged that the relevant standard sample is not present, the process operation jumps to a step S8.

Figure 9:
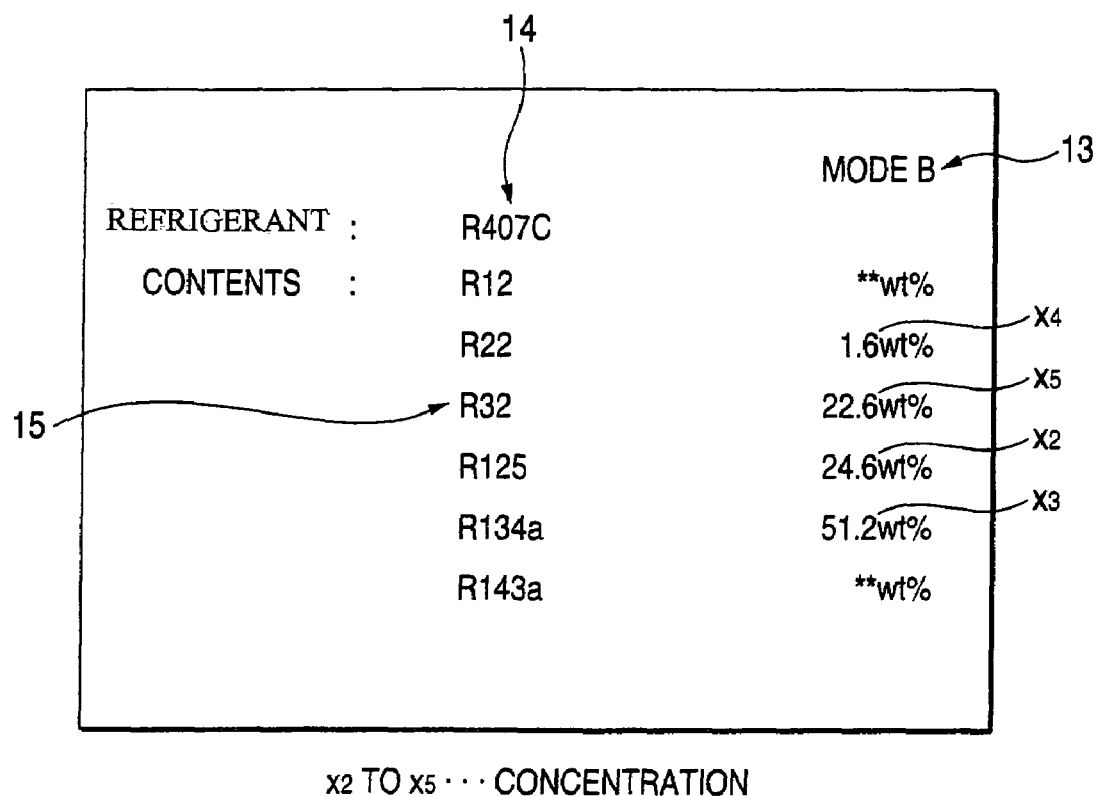
FIG. 9 is a diagram for indicating a display example of an analysis result.

In other words, the step S8 is such a step in which the respective component concentration $x_1$ to $x_7$ of the mixed fluorocarbon is directly displayed on the display portion 7. It should be noted that in FIG. 9, the calculation mode display portion 13 indicates a measurement result obtained by the B mode, and the refrigerant display portion 14 displays a name of such a sample ("R407C" in this example) which is selected at the previous step 4 and resembles the relevant standard sample at the highest degree.

Figure 10:
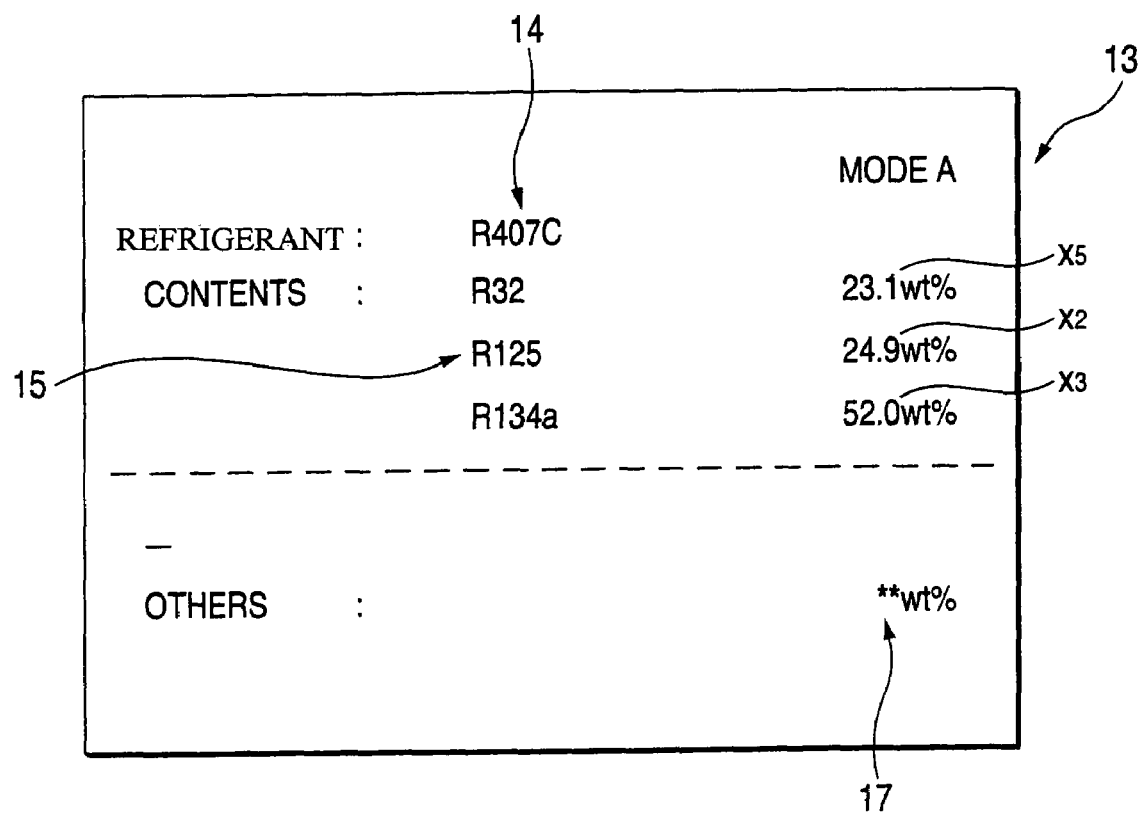
FIG. 10 is a diagram for indicating a display example of an analysis result.

On the other hand, a step "S9" corresponds to a step for displaying respective component concentration $x_1$ to $x_7$ on the display unit 7 in such a case that it is so judged in the previous step S7 that the component ratio is identical to that of the standard sample. FIG. 10 is a diagram for indicating an example of a screen displayed in the step S9. In FIG. 10, reference numeral 17 indicates a display portion which displays thereon weight % of other components, very small amounts of which are contained in the standard sample. In this example, this display portion 17 indicates that these very small amounts are substantially equal to detection limit amounts. Also, the calculation mode display portion 13 indicates a measurement result acquired by the A mode, and also indicates that the analyzing operation by the multi-component analyzing apparatus 1 could be carried out in the highest precision.

As indicated in FIG. 10, at such a stage that the measurement result could be acquired in the A mode in the highest precision, the mode display is arbitrarily switched between the B mode and the A mode by using the manual switching buttons 8e and 8d shown in FIG. 1, so that the concentration of the respective components may be confirmed.

Figure 11:
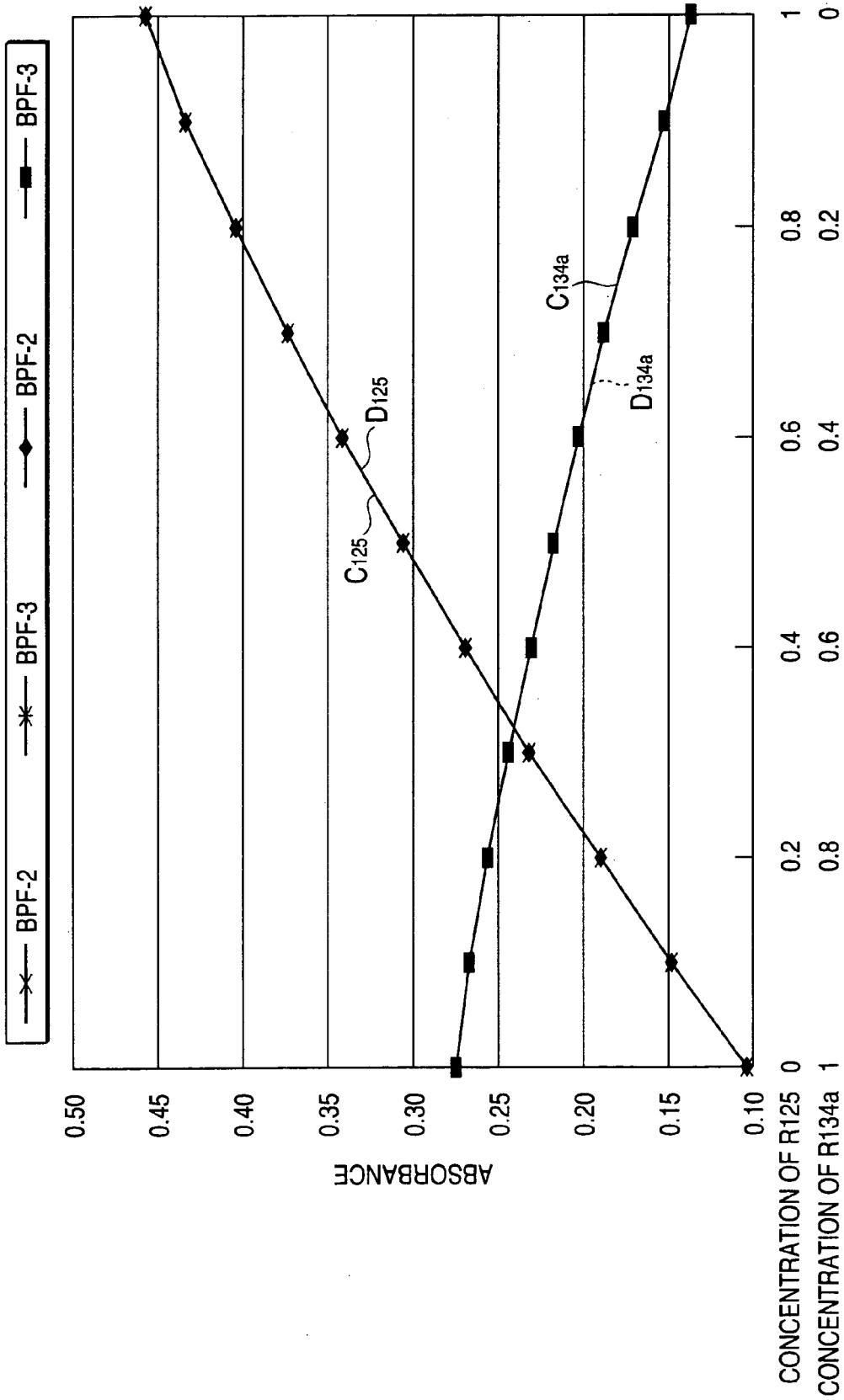
FIG. 11 is a diagram for confirming precision of simultaneous equations employed in the multi-component analyzing apparatus of the present invention.
Figure 12:
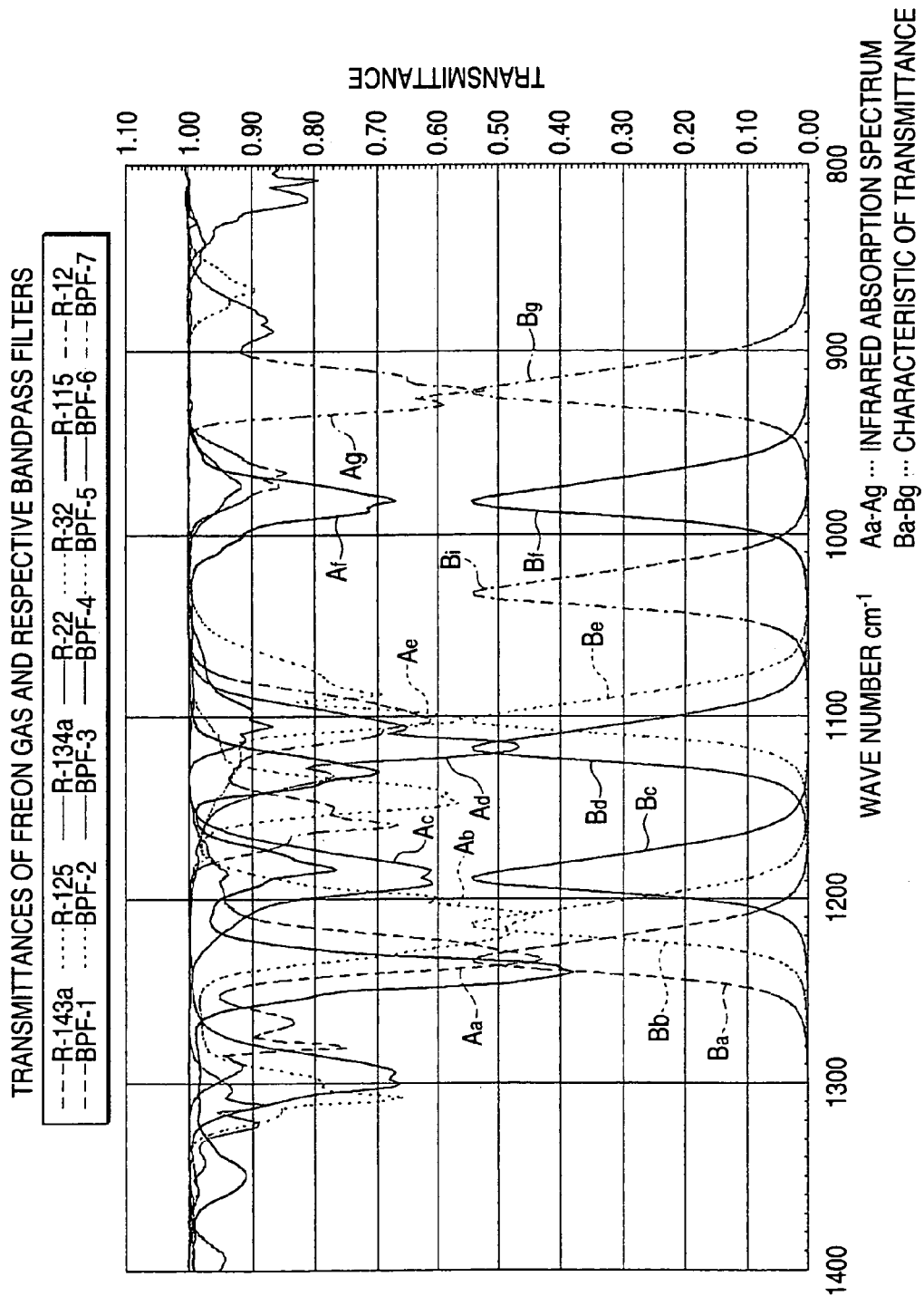
FIG. 12 is a diagram for comparing transmittances of light of the respective measuring-subject components and characteristics of the respective bandpass filters.

FIG. 11 is a diagram for indicating such an example as to both measurement values (absorbances) $y_2$, $y_3$, and calculation values $f_2(0, x_2, x_3, 0, 0, 0, 0)$, and $f_3(0, x_2, x_3, 0, 0, 0, 0)$. That is, in the above-described example, the measurement values $y_2$ and $y_3$ are actually measured while concentration of fluorocarbon (R125, R134a) of two components is varied, and these calculation values $f_2$ and $f_3$ are obtained by substituting the concentration $x_2$ and $x_3$ for the formula (6).

In FIG. 11, symbol "X" shows an actually-measured value of the absorbances $y_2$; symbol "*" denotes an actually-measured value of the absorbance $y_3$; symbol "♦" which is substantially overlapped with the symbol "X" represents a value of the calculation formula (containing mutual interference correction) $f_2(0, x_2, x_3, 0, 0, 0, 0)$; and also, symbol "■" which is substantially overlapped with the symbol "X" shows a value of the calculation formula (containing mutual interference correction) $f_3(0, x_2, x_3, 0, 0, 0, 0)$. Also, curves "$C_{125}$" and "$C_{134a}$" in FIG. 11 correspond to such curves made by connecting the respective points of the above-explained calculation values $f_2(0, x_2, x_3, 0, 0, 0, 0)$ and $f_3(0, x_2, x_3, 0, 0, 0, 0)$, whereas curves "$D_{125}$" and "$D_{134a}$" correspond to such curves formed by connecting the respective points of the measurement values $Y_2$ and $y_3$.

Figure 13:
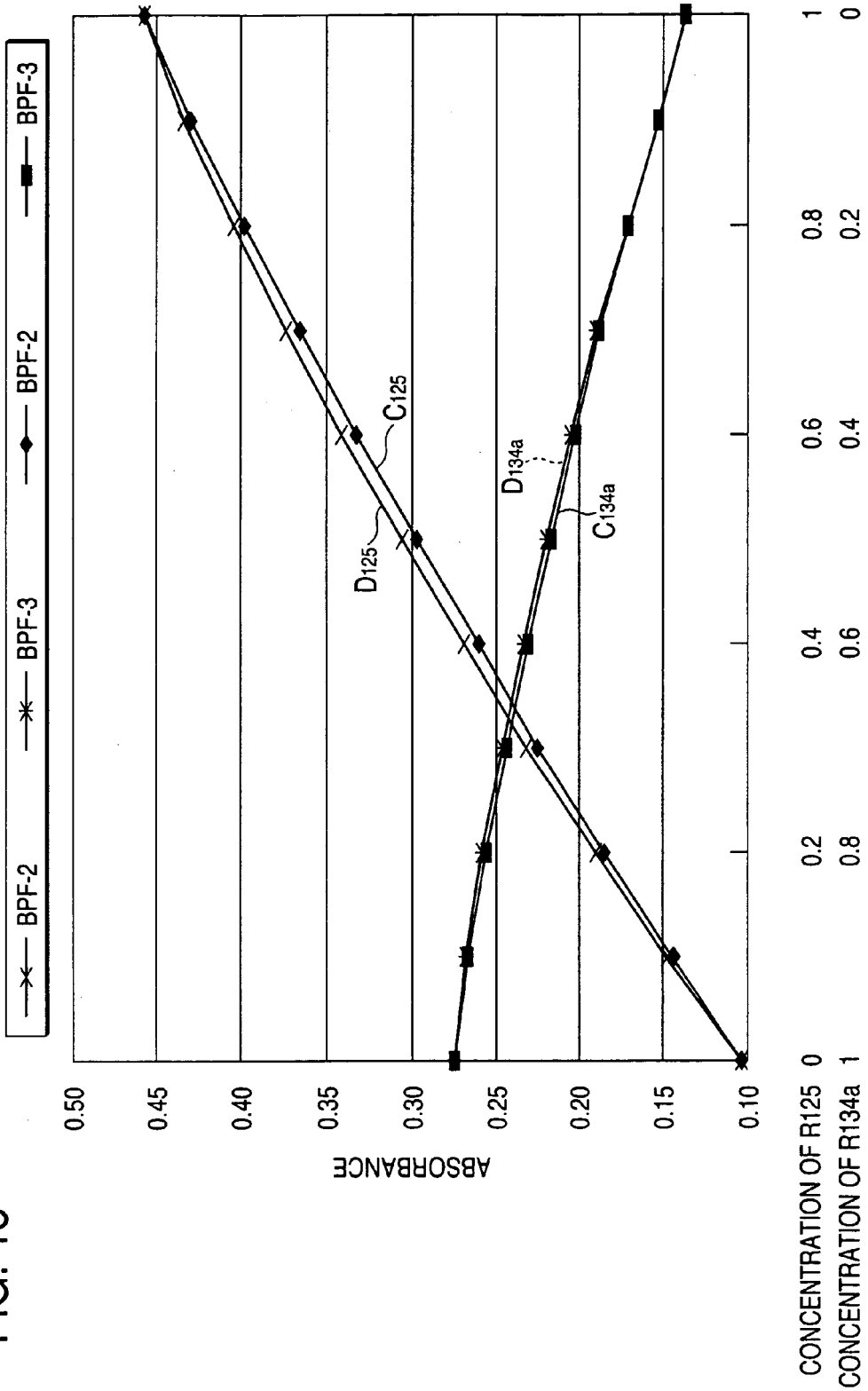
FIG. 13 is a diagram for confirming the errors occurred in the simultaneous equations employed in the conventional multi-component analyzing apparatus.

As indicated in FIG. 11, the actually-measured values of the measurement values $y_2$ and $y_3$ are essentially overlapped with the values of the calculation formulae $f_2(0, x_2, x_3, 0, 0, 0, 0)$ and $f_3(0, x_2, x_3, 0, 0, 0, 0)$, and also, substantially no error is present between these values. As apparent from a comparison result between FIG. 11 and FIG. 13, the analyzing precision of the present invention 10 times, or higher than that of the prior art can be improved. In other words, while the complexness of the analyzing calculation is kept in minimum degree, the sufficiently high precision can be achieved.

Precisely speaking, since the calculation using the above-described formula (6) is carried out, the magnitudes of errors can be reduced from several weight % (prior art) to approximately 0.2 to 0.3 weight % (present invention), which represents that the measuring operation can be carried out in considerably high precision, as compared with the measurement precision of the prior art. In addition, since the calculation using the above-explained formula (7) is carried out, the errors can be further decreased, and thus, may be reduced smaller than, or equal to 0.1 weight %.

Furthermore, the calculation is carried out by employing such a formula obtained by expanding the formula (3) instead of the calculation using the above-described formula (6), so that resulting precision may be furthermore improved. In this case, for example, various modifications may be conceived, for instance, higher dimensional terms higher than, or equal to the three-dimensional term may be omitted.

In any of these cases, there is such a common point arranged in the multi-component analyzing apparatus 1 of the present invention. That is, the calculating process unit 6 may execute the analyzing process program P capable of executing the above-described analyzing operation by solving the simultaneous equation (formula (3), formula (4) etc.) which are constituted by such equations having the mutual interference correction terms used to correct the interference adverse influences among the respective measuring-subject components. Also, even when another simultaneous equations different from the above-explained formulae (3) and (4) are employed, since the mutual interference correction term is provided, a similar effect to that of the above-explained example may be achieved.

As previously explained, in accordance with the multi-component analyzing apparatus of the present invention, even in such a case that the measuring-subject components which mutually may give the interference adverse influences to each other are mixed with each other, the analyzing operation can be carried out in very high precision. Thus, the multi-component analyzing apparatus whose calculation precision is considerably improved can be provided.

Second Embodiment

Figure 14:
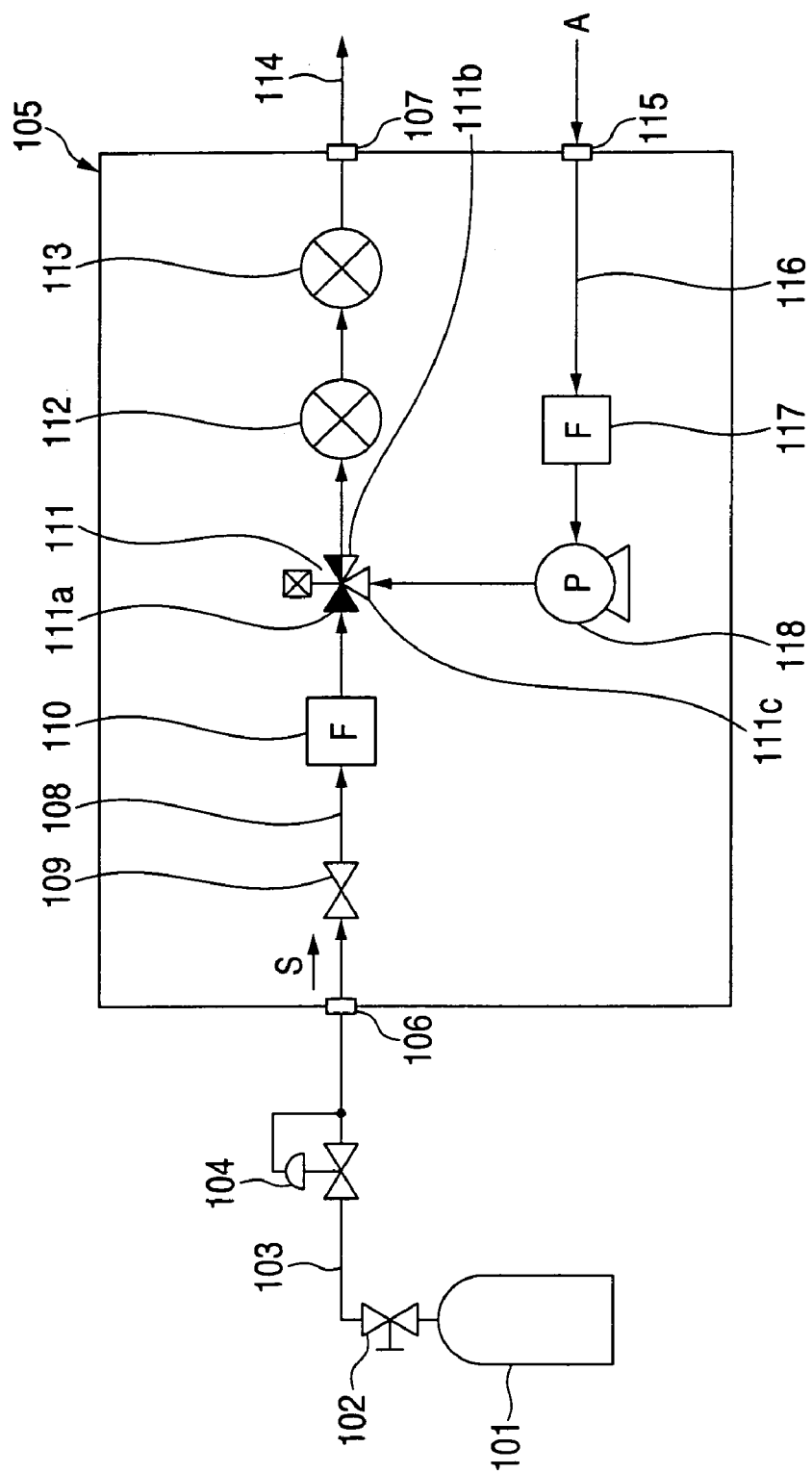
FIG. 14 schematically indicates an example of an arrangement of a mixed-refrigerant analyzing apparatus according to the present invention.
Figure 15:
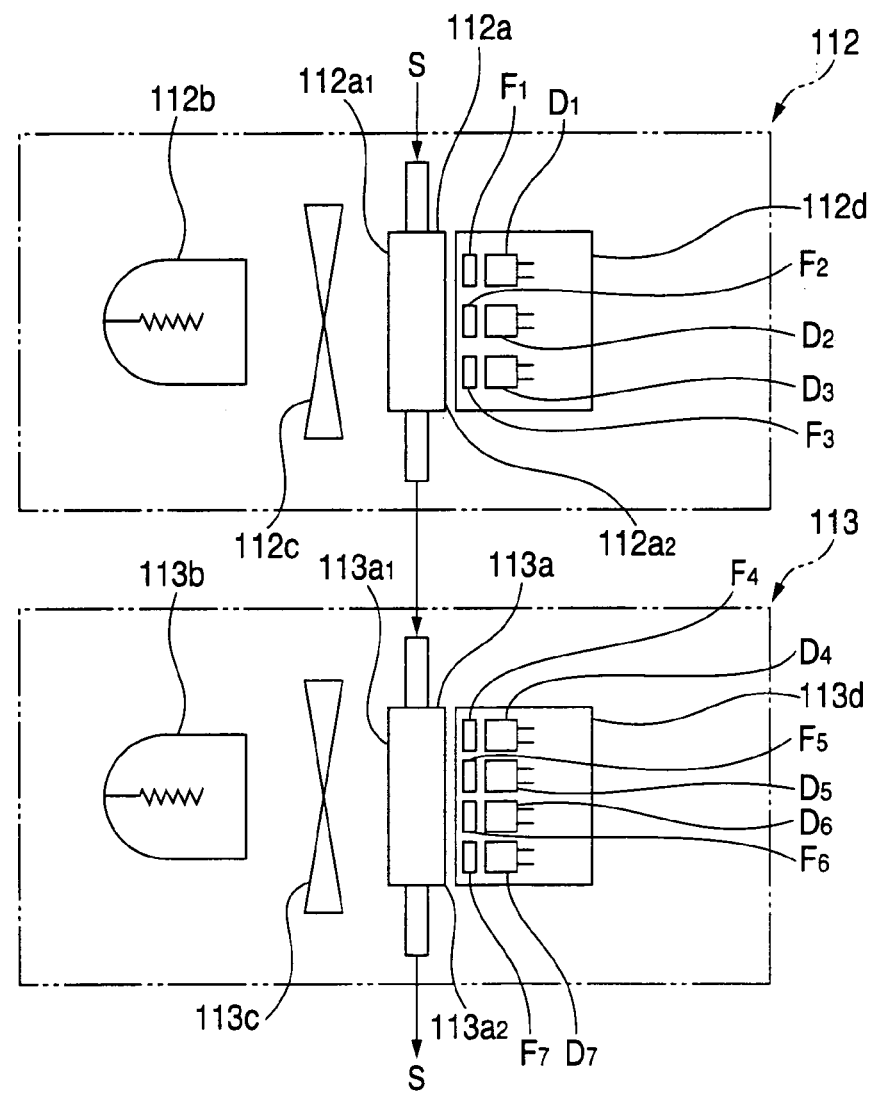
FIG. 15 schematically represents an arrangement of an analyzing unit of the infrared gas analyzing meter.

Referring now to drawings, a mixed-refrigerant analyzing apparatus of the present invention will be described in detail. FIG. 14 to FIG. 16 indicates one embodiment mode of the present invention. First, FIG. 14 schematically shows a structural example of a mixed-refrigerant analyzing apparatus according to the present invention. In this drawing, reference numeral 101 shows Bombe which has stored thereinto a mixed refrigerant functioning as sample gas "S", and reference numeral 102 represents a Bombe valve. Reference numeral 103 indicates a sample gas supplying path used to connect Bombe 101 to a mixed-refrigerant analyzing apparatus 105 (will be discussed later). This sample gas supplying path 103 is equipped with a pressure control device 104.

Reference numeral 105 shows a mixed-refrigerant analyzing apparatus 105. This mixed-refrigerant analyzing apparatus 105 is arranged as follows. That is, for instance, reference numerals 106 and 107 represent a gas inlet and a gas outlet, respectively, which are formed in the mixed-refrigerant analyzing apparatus 105. A downstream end of the sample gas supplying path 103 is connected to the gas inlet 106. Reference numeral 108 represents a gas path formed between the gas inlet 106 and the gas outlet 107. The sample gas S supplied from the gas inlet 106 passes through this gas path 108. A flow-rate controlling needle valve opening/closing-valve 109, an oil filter 110, a three-way electromagnetic valve 111, a gas analyzing unit 112, and another gas analyzing unit 113 are provided in this order from an upstream side of the gas path 108. The three-way electromagnetic valve 111 is interposed in the gas path 108 in such a manner that a first port 111a which is closed when the power supply is turned OFF is connected to the oil filter 110, and a normally-open second port 111b is connected to the gas analyzing unit 112. It should be noted that reference numeral 114 shows a gas ejection (discharge) path connected to the gas outlet 107, and a downstream side of this gas ejection path 114 is connected to a properly-provided gas collecting unit (not shown).

The above-described gas analyzing units 112 and 113 analyze ratios of respective refrigerant components contained in a mixed refrigerant by utilizing the NDIR method, and are arranged as shown in, for example, FIG. 15. In other words, one gas analyzing unit 112 is arranged by a cell 112a, an infrared light source 112b and a chopper 112c, which are provided on the side of one window $112a_1$ of this cell 112a, and also a detecting unit 112d provided on the side of the other window $112a_2$ of the cell 112a. The other gas analyzing unit 113 is arranged by a cell 113a, an infrared light source 113b and a chopper 113c, which are provided on the side of one window $113a_1$ of this cell 113a, and also a detecting unit 113d provided on the side of the other window $113a_2$ of the cell 113a.

Then, the cell 112a of the above-explained one gas analyzing unit 112 is series-connected to the cell 113a of the other gas analyzing unit 113. The sample gas S is supplied via the three-way electromagnetic valve 111 to one cell 112a positioned on an upstream side, whereas the sample gas S is supplied via this cell 112a to the other cell 113a which is series-connected to the cell 112a in such a manner that this cell 113a is located on the downstream side of this cell 112a.

Figure 16A:
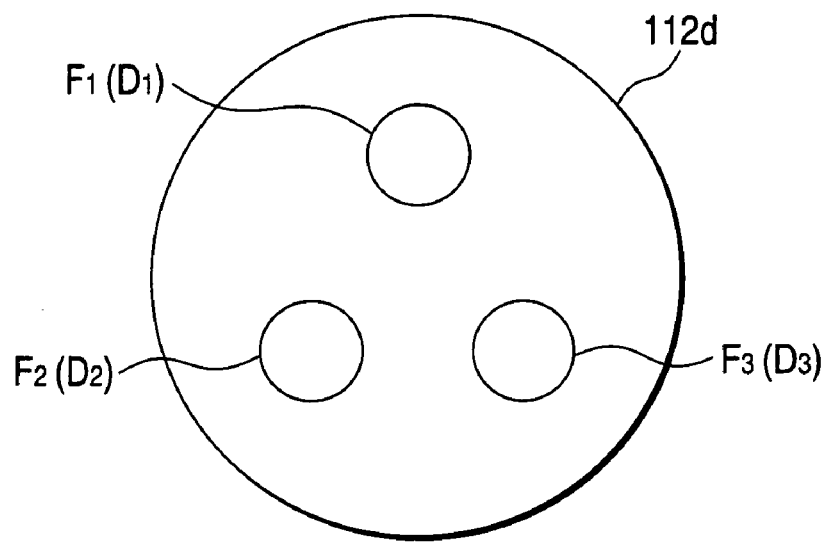
FIGS. 16A and 16B schematically show an arrangement of a detecting unit of the infrared gas analyzing unit.
Figure 16B:
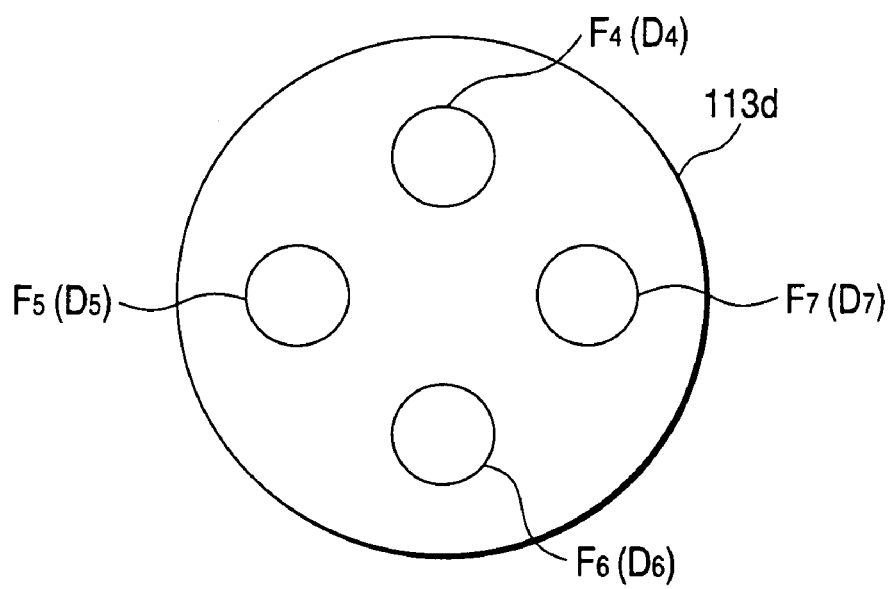

Also, the above-described detecting units 112d and 113d are arranged in order that for example, 7 pieces (7 sorts) of refrigerant components which are contained in the mixed refrigerant employed as the sample gas S can be detected by these two detecting units 112d and 113d. That is to say, in one detecting unit 112d, three pyroelectric detectors "$D_1$" to "$D_3$" and three bandpass filters "$F_1$" to "$F_3$" constitute pairs in correspondence with three sorts of refrigerant components (R143a, R125, R134a) among seven sorts of the above-described refrigerant components, and furthermore, as indicated in FIG. 16A, are arranged in such a manner that the circumference is equally divided by 3. Then, in the other detecting unit 113d, the four pyroelectric detectors "$D_4$" to "$D_7$" and four bandpass filters "$F_4$" to "$F_7$" constitute pairs in correspondence with the remaining four sorts of refrigerant components (R32, R115, R12, R22) among seven sorts of the above-described refrigerant components, and furthermore, as indicated in FIG. 16B, are arranged in such a manner that a circumference is equally divided by 4.

Then, the seven bandpass filters $F_1$ to $F_7$ employed in the above-described detecting units 112$d$ and 113$d$ are set in such a manner that infrared transmission wavelength ranges thereof are not adversely influenced by interference caused by other refrigerant components and S/N ratio is large. Also, the seven bandpass filters "$F_1$" to "$F_7$" are subdivided into two filter groups in response to absorbances of refrigerant components corresponding to the measuring subject components detected by the respective bandpass filters $F_1$ to $F_7$. Thus, the bandpass filters $F_1$ to $F_3$ corresponding to such refrigerant components whose absorbances are large are stored into the detecting unit 112$d$, whereas the bandpass filters $F_4$ to $F_7$ corresponding to such refrigerant components whose absorbances are small are stored into the detecting unit 113$d$. Furthermore, as to the seven bandpass filters $F_1$ to $F_7$, transmission central wave numbers thereof are set as shown in, for example, the below-mentioned table 4 in correspondence with the infrared absorption spectra of the seven refrigerant components.

TABLE 4

| | R143 | R125 | R134a | R32 | R115 | R12 | R22 |
|---|---|---|---|---|---|---|---|
| | | | | | | | unit: cm$^{-1}$ |
| central wave number | 1235 | 1215 | 1187 | 1083 | 981 | 920 | 813 |

Returning back to FIG. 14, reference numeral 115 indicates a zero gas inlet formed in the mixed-refrigerant analyzing apparatus 105. A zero gas supplying path 116 is formed between this zero gas inlet 115 and a third port 111$c$ which is opened when the power supply of the three-way electromagnetic valve 111 is turned OFF. A filter 117 and a suction pump 118 are provided in this order within this zero gas supplying path 116. Then, this zero gas supplying path 116 supplies zero gas "Z" to the cells 112$a$ and 113$a$ of the gas analyzing units 112 and 113 having the above-described structures via the three-way electromagnetic valve 111. In this embodiment mode, the mixed-refrigerant analyzing apparatus 105 is arranged in such a manner that air "A" is conducted from the zero gas inlet 115, this conducted air A is filtered by the filter 117 to become clean air, and then, this clean air may become the zero gas Z.

Although not shown in the drawing, a calculation control apparatus (for example, personal computer) is provided in the above-described mixed-refrigerant analyzing apparatus 105, while this calculation control apparatus may sequentially control the respective structural units of this analyzing apparatus 105, and may perform concentration calculations (component ratio calculations) of a plurality (seven refrigerant components in this example) of refrigerant components based upon gas analysis results outputted from the gas analyzing units 112 and 113.

A description will now be made of measuring operations of a mixed refrigerant with employment of the mixed-refrigerant analyzing apparatus 105 with employment of the above-explained arrangement. The measurement key of the calculation control apparatus is manually turned ON so as to turn ON the three-way electromagnetic valve 111. Then, under this condition, the Bombe value 102 is manually opened in order to supply a mixed refrigerant stored in Bombe 101 as the sample gas "S" to the mixed-refrigerant analyzing apparatus 105 of this embodiment mode of the present invention. The sample gas S supplied to the mixed-refrigerant analyzing apparatus 105 is entered through the needle valve 109, the oil filter 110, and the three-way electromagnetic valve 111 to the cell 112$a$ of the gas analyzing unit 112 provided on the upperstream side. Then, the sample gas S which has passed through this cell 112$a$ is entered into the cell 113$a$ of the gas analyzing unit 113 provided on the downstream side. In these gas analyzing units 112 and 113, while the sample gas S is supplied to the cells 112$a$ and 113$a$, the analyzing operation of the sample gas S is carried out. Since this sample gas analyzing operation is carried out, a sensor signal rises, and thereafter, the respective gas analyzing units 112 and 113 execute sampling operations of data. As a consequence, a measurement signal "s" is obtained every refrigerant component from each of the gas analyzing units 112 and 113. Then, the sample gas S outputted from the gas analyzing unit 113 provided on the downstream side is entered from the gas outlet 107 into the gas ejection path 114, and thereafter, is collected. Also, after the three-way electromagnetic valve 111 has been turned ON for a predetermined time duration, this three-way electromagnetic valve 111 is turned OFF. After this three way electromagnetic valve 111 has been turned OFF, and further, a certain time has elapsed, the Bombe valve 102 is manually closed.

Then, when the suction pump 118 is turned ON, the zero gas Z is entered from the zero gas supplying path 116 via the three-way electromagnetic valve 111 to the cell 112$a$ of the gas analyzing unit 112 provided on the upper stream side, and the zero gas Z which has passed through this cell 112$a$ is entered into the cell 113$a$ of the gas analyzing unit 113 provided on the downstream side, and also, the sensor signal which has risen falls downwardly. In the gas analyzing units 112 and 113, while the zero gas Z is supplied to the cells 112$a$ and 113$a$, a zero measuring operation based upon the zero gas "Z" is carried out. As a result, a zero signal "z" is obtained every refrigerant component from each of the gas analyzing units 112 and 113. Then, the zero gas Z which has sequentially flown through the gas analyzing units 112 and 113 is entered from the gas outlet 107 to the gas ejection path 114, and thereafter, is collected.

Then, in the calculation control apparatus, a ratio of the plural refrigerant components contained in the sample gas S may be obtained by, for example, calculating a ratio [log (s/z)] based upon the measurement signals "s($s_2$ to $s_7$)" outputted from a plurality of pyroelectric detectors $D_1$ to $D_7$ which are provided in correspondence with a plurality of refrigerant components acquired when the sample gas is measured, and also, the zero signals "z($z_1$ to $z_7$)" derived from the pyroelectric detectors $D_1$ to $D_7$, which are acquired when the zero measuring operation is carried out.

Figure 17:
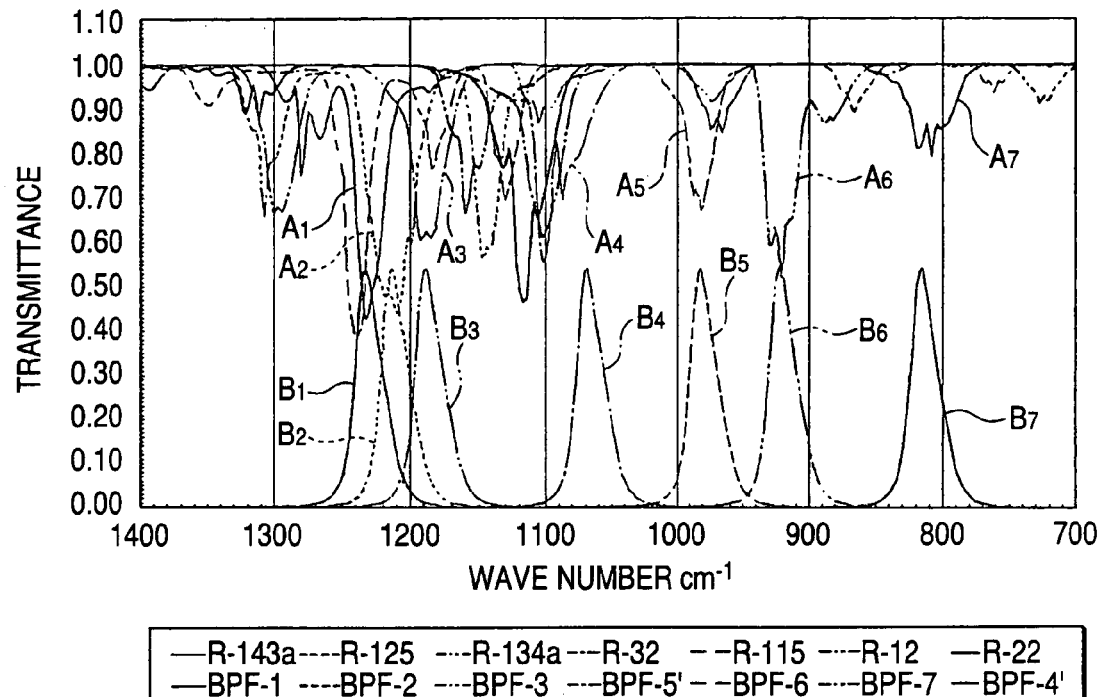
FIG. 17 is a diagram for indicating an example of infrared transmittances and infrared transmission characteristics of respective bandpass filters, employed in the mixed-refrigerant analyzing apparatus.
Figure 19A:
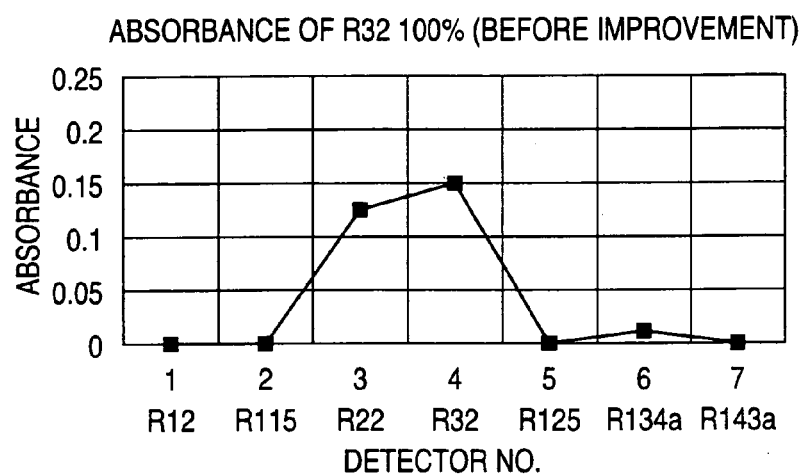
FIGS. 19A to 19D are diagrams for explaining mutual interference occurred in the refrigerant components R32 and R22.
Figure 19B:
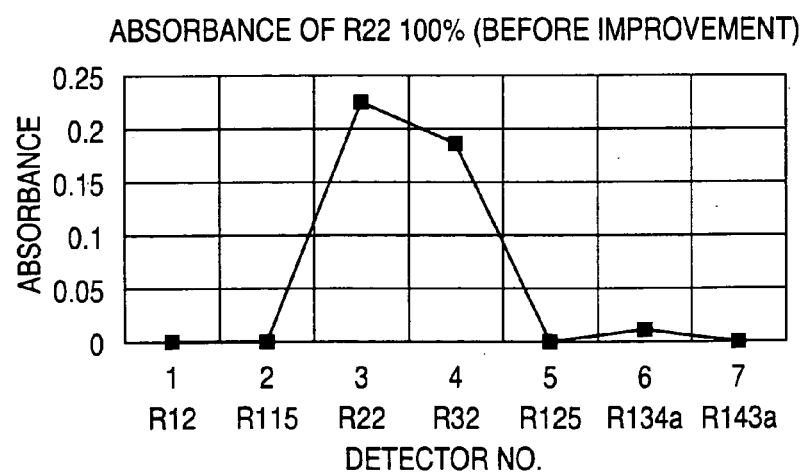
Figure 19C:
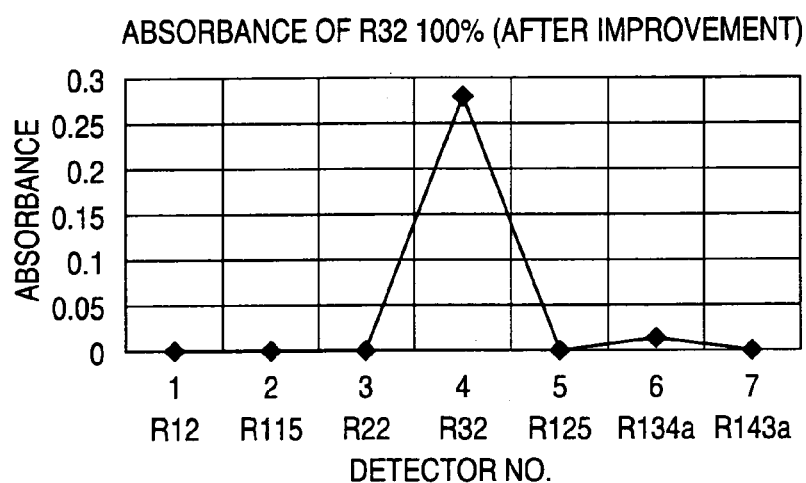
Figure 19D:
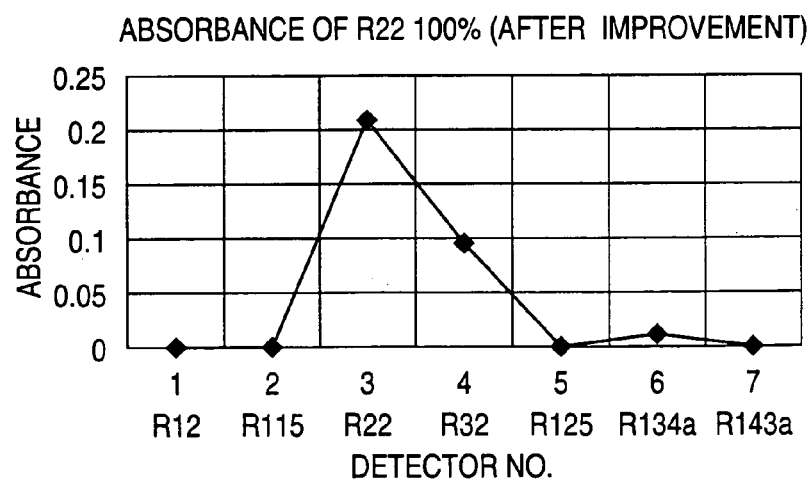
Figure 20:
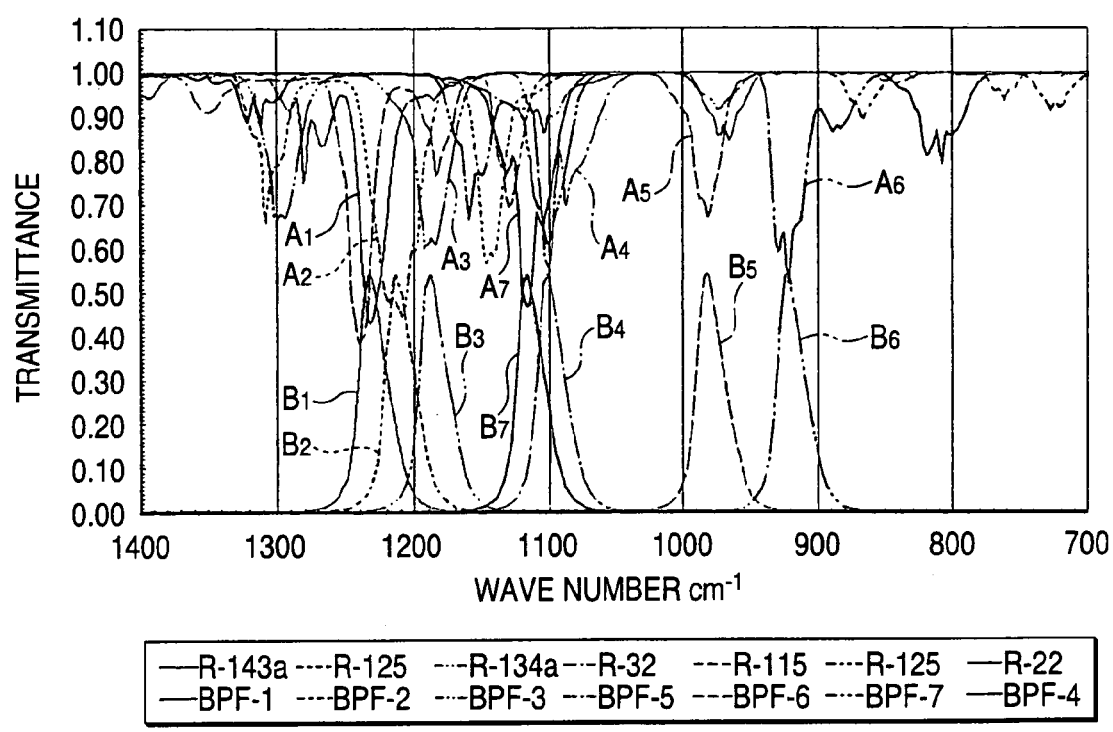
FIG. 20 is a diagram for indicating the infrared transmittances and the infrared transmission characteristics of the respective bandpass filters, employed in the conventional mixed-refrigerant analyzing apparatus.

As previously explained, in the mixed-refrigerant analyzing apparatus of this embodiment mode, the infrared transmission central wave numbers of the seven bandpass filters $F_1$ to $F_7$ are set as indicated in the above-described table 4, and are employed so as to detect the seven sorts of refrigerant components R143a, R125, R134a, R32, R115, R12, and R22 contained in the sample gas S. As a consequence, as shown in FIG. 17, infrared absorption spectra (namely, curves denoted by symbols "$A_1$" to "$A_7$" in this drawing) of the above-explained seven refrigerant components may mutually correspond to infrared transmission characteristics (namely, curves indicated by symbols "$B_1$" to "$B_7$" in this drawing) of the respective bandpass filters $F_1$ to $F_7$. Accordingly, deferent from the conventional mixed-refrigerant analyzing apparatus, the mixed-refrigerant analyzing apparatus of the embodiment mode can analyze the plural refrigerant components of the mixed refrigerant in higher precision while suppressing the mutual interference caused by the plural refrigerant components as much as possible. Also, as indicated in FIG. 19C and FIG. 19D, the respective absorbances of the refrigerant components R32 and R22 do not receive the adverse influences from each other, so that such absorbance characteristics having clear steep degrees can be obtained.

Measurement errors produced when the infrared transmission central wave numbers of the seven bandpass filters $F_1$ to $F_7$ are set to those shown in the above-described table 4 are given as shown in the below-mentioned table 5.

TABLE 5

|  | R143a | R125 | R134a | R32 | R115 | R12 | R22 |
|---|---|---|---|---|---|---|---|
| Prior art | less than 1% | 1.5% | less than 1% | 2.6% | less than 1% | 1.5% | 3.9% |
| embodiment | less than 1% | less than 1% | less than 1% | less than 1% | less than 1% | less than 1% | less than 1% |

In the above table 5, numerals of an upper stage are equal to those of the table 2 which are again described. As easily understood from this table 5, the mutual interference degrees caused by the seven refrigerant components can be suppressed as many as possible, and the respective refrigerant components can be analyzed in higher precision.

It should be noted that the central wave numbers of the seven bandpass filters $F_1$ to $F_7$ are not limited only to the central wave numbers shown in the above-described table 4. Alternatively, as to the respective central wave numbers, for example, a slight allowable range may be provided as indicated in the below-mentioned table 6.

TABLE 6 unit: cm$^{-1}$

|  | R143a | R125 | R134a | R32 | R115 | R12 | R22 |
|---|---|---|---|---|---|---|---|
| upper limit value of central wave number | 1235 | 1220 | 1192 | 1088 | 1000 | 933 | 820 |
| lower limit value of central wave number | 1222 | 1205 | 1180 | 1065 | 981 | 908 | 798 |

On the other hand, in the above-described embodiment mode, the mutual interference occurred in the refrigerant components R32 and R22 has been described. In particular, the central wave numbers of the bandpass filters $F_4$ and $F_7$ corresponding to these refrigerant components R32 and R22 have been changed to be again set. Alternatively, as to other refrigerant components R143a and R125, the central wave numbers of the bandpass filters $F_1$ and $F_4$ corresponding to these refrigerant components may be changed to be again set. The below-mentioned table 7 indicates an example of upper limit values and lower limit values as to the central wave numbers of the seven bandpass filters $F_1$ to $F_7$ in this alternative case.

TABLE 7 unit: cm$^{-1}$

|  | R143a | R125 | R134a | R32 | R115 | R12 | R22 |
|---|---|---|---|---|---|---|---|
| upper limit value of central wave number | 1269 | 1151 | 1192 | 1088 | 1000 | 933 | 820 |
| lower limit value of central wave number | 1263 | 1137 | 1180 | 1065 | 981 | 908 | 798 |

Figure 18:
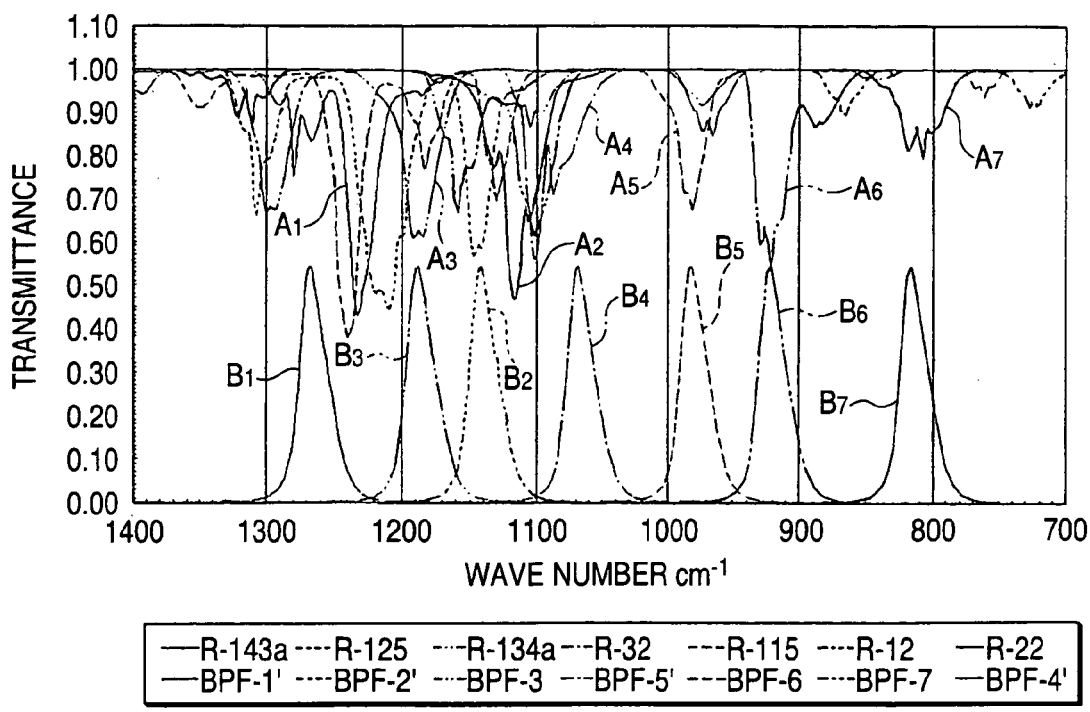
FIG. 18 is a diagram for indicating another example of infrared transmittances and infrared transmission characteristics of respective bandpass filters, employed in the mixed-refrigerant analyzing apparatus.

Since the infrared transmission central wave numbers of the seven bandpass filters $F_1$ to $F_7$ are set as indicated in the above-described table 7, and are employed so as to detect the seven sorts of refrigerant components R143a, R125, R134a, R32, R115, R12, and R22, as shown in FIG. 18, infrared absorption spectra (namely, curves denoted by symbols "$A_1$" to "$A_7$" in this drawing) of the above-explained seven refrigerant components may mutually correspond to infrared transmission characteristics (namely, curves indicated by symbols "$B_1$" to "$B_7$" in this drawing) of the respective bandpass filters $F_1$ to $F_7$. Therefore, the mixed-refrigerant analyzing apparatus of the embodiment mode can analyze the plural refrigerant components of the mixed refrigerant in higher precision while suppressing the mutual interference caused by the plural refrigerant components as much as possible.

Alternatively, both the upper limit values and the lower limit values of the central wave numbers of the bandpass filters $F_1$ and $F_2$ used to detect the refrigerant components R143a and R125 may be set as follows. That is to say, (1) as to the refrigerant component R143a, the upper limit value and the lower limit value of the bandpass filter $F_1$ are set to 1222 to 1235 cm$^{-1}$, whereas with respect to the refrigerant component R125, the upper limit value and the lower limit value of the bandpass filter $F_2$ are set to 1137 to 1151 cm$^{-1}$.

Otherwise, (2) as to the refrigerant component R143a, the upper limit value and the lower limit value of the bandpass filter $F_1$ are set to 1263 to 1269 cm$^{-1}$, whereas with respect to the refrigerant component R125, the upper limit value and the lower limit value of the bandpass filter $F_2$ are set to 1205 to 1220 cm$^{-1}$.

Then, in any one of the above-described alternative cases (1) and (2), both the upper limit values and the lower limit values of the central wave numbers of the bandpass filters $F_3$ to $F_7$ used to detect other five refrigerant components (R134a, R32, R115, R12, R22) are made equal to those shown in either the table 6 or the table 7.

In any one of these alternative cases, the infrared absorption spectra of the plural refrigerant components may mutually correspond to the infrared transmission characteristics of the respective bandpass filters, so that these plural refrigerant components may be analyzed in higher precision, while the mutual interference may be suppressed as much as possible.

It should be noted that in the mixed-refrigerant analyzing apparatus with employment of the above-explained arrangement, both the bandpass filters $F_1$ to $F_7$ and the detectors $D_1$ to $D_7$, which correspond to the respective refrigerant components, are classified into two groups in response to the absorbances of the respective refrigerant components, and also, the cells 112a and 113a having the different cell lengths in correspondence with the respective groups. In this case, the cell length of the cell 112a corresponding to the detecting unit 112d may be made shorter than the cell length of the cell 113a corresponding to the detecting unit 113d so as to control the absorbance levels between the respective groups, while the detecting unit 112d stores thereinto the bandpass filters $F_1$ to $F_3$ and the detectors $D_1$ to $D_3$, which are employed so as to detect the refrigerant components having the large absorbances, whereas the detecting unit 113d stores thereinto the bandpass filters $F_4$ to $F_7$ and the detectors $D_4$ to $D_7$ which are employed so as to detect the refrigerant components having the small absorbances. In such a case, linearity of the measuring sensitivities as to all of the refrigerant components may be maintained within a necessary range. As a result, measurement results may be obtained in higher precision.

It should also be noted that in the above-described embodiment mode, such an example has been exemplified that the seven refrigerant components are present in the mixed refrigerant, and all of these seven refrigerant components are analyzed. However, the present invention is not limited only to this exemplified example, but may be modified. For example, a mixed refrigerant may be constituted by two, or more sorts of refrigerant components. Also, in the above-explained embodiment mode, the mixed-refrigerant analyzing apparatus 105 is arranged by a plurality of gas analyzing units 112 and 113. Instead of this arrangement, as a single gas analyzing unit, a single cell having a plurality of cell lengths may be employed in this gas analyzing unit.

As previously explained, in accordance with the mixed-refrigerant analyzing apparatus of the present invention, a plurality of refrigerant components corresponding to the measuring-subject components can be analyzed in higher precision, while the mutual interference caused by these plural refrigerant components can be suppressed as much as possible.

What is claimed is:

1. A multi-component analyzing apparatus in which infrared light is irradiated to a measuring-subject sample which is constituted by either measuring-subject components whose sorts or quantities are limited or by a mixed article made of said measuring-subject components; intensity of infrared light having respective wavelength ranges which are fitted to infrared absorption spectra of the respective measuring-subject components among such infrared light penetrated through the measuring-subject sample is measured by employing a plurality of detectors corresponding thereto; and said multi-component analyzing apparatus includes a calculation processing unit for analyzing the infrared light intensity of the respective wavelength ranges so as to acquire concentration of the respective measuring-subject components;

wherein the calculation processing unit is operative to execute an analyzing process program for executing analysis operations of the concentration of the respective measuring-subject components by solving simultaneous equations which are constituted by equations having mutual interference correction terms used to correct interference adverse influences occurred among the respective measuring-subject components, wherein said mutual interference correction term includes a product made by multiplying a product of concentration of at least two measuring-subject components by one, or more mutual interference correction coefficients.

2. A multi-component analyzing apparatus as claimed in claim 1, wherein said mutual interference correction coefficient is such a value obtained by dividing a difference by said product of the concentration of said two measuring-subject components, while said difference is calculated between a measurement value obtained by measuring a calibration-purpose sample formed by mixing two measuring-subject components with each other in a preselected ratio, and such a value obtained by substituting the concentration of said two measuring-subject components for such equations from which the mutual interference correction terms have been eliminated among said equations.

3. A multi-component analyzing apparatus in which infrared light is irradiated to a measuring-subject sample which is constituted by either measuring-subject components whose sorts or quantities are limited or by a mixed article made of said measuring-subject components; intensity of infrared light having respective wavelength ranges which are fitted to infrared absorption spectra of the respective measuring-subject components among such infrared light penetrated through the measuring-subject sample is measured by employing a plurality of detectors corresponding thereto; and said multi-component analyzing apparatus includes a calculation processing unit for analyzing the infrared light intensity of the respective wavelength ranges so as to acquire concentration of the respective measuring-subject components;

wherein the calculation processing unit is operative to execute an analyzing process program for executing analysis operations of the concentration of the respective measuring-subject components by solving simultaneous equations which are constituted by equations having mutual interference correction terms used to correct interference adverse influences occurred among the respective measuring-subject components, wherein said equations are multi-dimensional equations; and said analyzing process program executes a stepwise calculation processing operation by which the concentration of the respective measuring-subject components is analyzed by employing simultaneous equations which are arranged by one-dimensional equations other than said multi-dimensional equations so as to calculate approximated values as to the concentration of said respective measuring-subject components, and said multi-dimensional simultaneous equations are converged by employing said approximated values.

4. A multi-component analyzing apparatus in which infrared light is irradiated to a measuring-subject sample which is constituted by either measuring-subject components whose sorts or quantities are limited or by a mixed article made of said measuring-subject components; intensity of infrared light having respective wavelength ranges which are fitted to infrared absorption spectra of the respective measuring-subject components among such infrared light penetrated through the measuring-subject sample is measured by employing a plurality of detectors corresponding thereto; and said multi-component analyzing apparatus includes a calculation processing unit for analyzing the infrared light intensity of the respective wavelength ranges so as to acquire concentration of the respective measuring-subject components;

wherein the calculation processing unit is operative to execute an analyzing process program for executing analysis operations of the concentration of the respective measuring-subject components by solving simultaneous equations which are constituted by equations having mutual interference correction terms used to correct interference adverse influences occurred among the respective measuring-subject components, wherein said calculation processing unit owns a standard sample correction coefficient which corresponds to either a ratio or a difference between measurement values of the respective detectors obtained by that while either standard samples made of single measuring-subject components or standard samples formed by mixing a plurality of measuring-subject components in predetermined concentration is employed, the respective standard samples are measured, and calculation values obtained by substituting the concentration of said standard samples for said simultaneous equations, and said standard sample correction coefficient has been stored in relation to each of said standard samples in order to further correct said simultaneous equations; and also said analyzing process program executes the analyzing process operation in the case that while the concentration of the respective measuring-subject components acquired by said analyzing process operation is compared with the concentration of said standard sample, when the relevant standard sample is present, the standard sample correction coefficient related to said relevant standard sample is employed so as to execute said analyzing process operation.

5. A mixed-refrigerant analyzing apparatus comprising:
a cell to which a mixed refrigerant containing a plurality of refrigerant components is supplied as sample gas;
an infrared light source for irradiating infrared light to said cell;
a plurality of bandpass filters for penetrating therethrough infrared light having wavelengths which are fitted to infrared absorption spectra of said respective refrigerant components among infrared light which has penetrated said cell;
a plurality of detectors for measuring intensity of the infrared light which has penetrated the respective bandpass filters; and
calculation processing unit for analyzing the infrared light intensity of the respective wavelength ranges so as to acquire concentration of the respective measuring-subject components;
wherein the calculation processing unit is operative to execute an analyzing process program for executing analysis operations of the concentration of the respective measuring-subject components by solving simultaneous equations which are constituted by equations having mutual interference correction terms used to correct interference adverse influences occurred among the respective measuring-subject components, and
wherein said mutual interference correction term includes a product made by multiplying a product of concentration of at least two measuring-subject components by one or more mutual interference correction coefficients.

6. A mixed-refrigerant analyzing apparatus comprising:
a cell to which a mixed refrigerant containing a plurality of refrigerant components is supplied as sample gas;
an infrared light source for irradiating infrared light to said cell;
a plurality of bandpass filters for penetrating therethrough infrared light having wavelengths which are fitted to infrared absorption spectra of said respective refrigerant components among infrared light which has penetrated said cell; and
a plurality of detectors for measuring intensity of the infrared light which has penetrated the respective bandpass filters;
wherein at least two bandpass filters are provided among such bandpass filters, the infrared transmission central wave numbers of which are set to 1222 to 1235 $cm^{-1}$, 1205 to 1220 $cm^{-1}$, 1180 to 1192 $cm^{-1}$, 1065 to 1088 $cm^{-1}$, 981 to 1000 $cm^{-1}$, 908 to 933 $cm^{-1}$ and 798 to 820 $cm^{-1}$, respectively, and
wherein each range of said infrared transmission central wave number is set on the basis of a suppression of mutual interference degrees caused by said components.

7. A mixed-refrigerant analyzing apparatus comprising:
a cell to which a mixed refrigerant containing a plurality of refrigerant components is supplied as sample gas;
an infrared light source for irradiating infrared light to said cell;
a plurality of bandpass filters for penetrating therethrough infrared light having wavelengths which are fitted to infrared absorption spectra of said respective refrigerant components among infrared light which has penetrated said cell; and
a plurality of detectors for measuring intensity of the infrared light which has penetrated the respective bandpass filters;
wherein at least two bandpass filters are provided among such bandpass filters, the infrared transmission central wave numbers of which are set to 1263 to 1269 $cm^{-1}$, 1137 to 1151 $cm^{-1}$, 1180 to 1192 $cm^{-1}$, 1065 to 1088 $cm^{-1}$, 981 to 1000 $cm^{-1}$, 908 to 933 $cm^{-1}$, and 798 to 820 $cm^{-1}$, respectively, and
wherein each range of said infrared transmission central wave number is set on the basis of a suppression of mutual interference degrees caused by said components.

8. A mixed-refrigerant analyzing apparatus comprising:
a cell to which a mixed refrigerant containing a plurality of refrigerant components is supplied as sample gas;
an infrared light source for irradiating infrared light to said cell;
a plurality of bandpass filters for penetrating therethrough infrared light having wavelengths which are fitted to infrared absorption spectra of said respective refrigerant components among infrared light which has penetrated said cell; and
a plurality of detectors for measuring intensity of the infrared light which has penetrated the respective bandpass filters;
wherein at least two bandpass filters are provided among such bandpass filters, the infrared transmission central wave numbers of which are set to 1222 to 1235 $cm^{-1}$, 1137 to 1151 $cm^{-1}$, 1180 to 1192 $cm^{-1}$, 1065 to 1088 $cm^{-1}$, 981 to 1000 $cm^{-1}$, 908 to 933 $cm^{-1}$, and 798 to 820 $cm^{-1}$, respectively, and
wherein each range of said infrared transmission central wave number is set on the basis of a suppression of mutual interference degrees caused by said components.

9. A mixed-refrigerant analyzing apparatus comprising:
a cell to which a mixed refrigerant containing a plurality of refrigerant components is supplied as sample gas;
an infrared light source for irradiating infrared light to said cell;
a plurality of bandpass filters for penetrating therethrough infrared light having wavelengths which are fitted to infrared absorption spectra of said respective refrigerant components among infrared light which has penetrated said cell; and
a plurality of detectors for measuring intensity of the infrared light which has penetrated the respective bandpass filters;
wherein at least two bandpass filters are provided among such bandpass filters, the infrared transmission central wave numbers of which are set to 1263 to 1269 $cm^{-1}$, 1205 to 1220 $cm^{-1}$, 1180 to 1192 $cm^{-1}$, 1065 to 1088 $cm^{-1}$, 981 to 1000 $cm^{-1}$, 908 to 933 $cm^{-1}$ and 798 to 820 $cm^{-1}$, respectively, and
wherein each range of said infrared transmission central wave number is set on the basis of a suppression of mutual interference degrees caused by said components.

10. A multi-component analyzing apparatus in which infrared light is irradiated to a measuring-subject sample which is constituted by either measuring-subject components whose sorts or quantities are limited or by a mixed article made of said measuring-subject components; intensity of infrared light having respective wavelength ranges which are fitted to infrared absorption spectra of the respective measuring-subject components among such infrared light penetrated through the measuring-subject sample is measured by employing a plurality of detectors corresponding thereto; and said multi-component analyzing apparatus includes a calculation processing unit for analyzing the infrared light intensity of the respective wavelength ranges so as to acquire concentration of the respective measuring-subject components;

wherein the calculation processing unit is operative to analyze the concentration of the respective measuring-subject components by solving simultaneous equations by calculating a product between a concentration of a measuring-subject sample and a constant according to the following equation:

$$y_i = \sum_{j=1}^{n} \left\{ (a_{ij}x_j + b_{ij}x_j^2 + c_{ij}x_j^3) \times \prod_{k=1}^{n} (1 + d_{ijk}x_k) \right\}$$

where the symbol "i" indicates a number of a detector, the symbol "j" represents a number of a measuring-subject component, the symbol "k" represents a number of a measuring-subject component which may interfere with a j-th measuring-subject component, the symbol "n" shows a total number of measuring-subject components, the symbol "$d_{ijk}$" denotes a mutual interference correction coefficient defined such that when j=k, the mutual interference correction coefficient "$d_{ijk}$" is equal to zero, and the symbols a, b and c represent constants.

11. The multi-component analyzing apparatus as recited in claim 10, wherein when the mutual interference correction term is limited by a product of the concentration of two measuring-subject components, the formula comprises:

$$y_i = \sum_{j=1}^{n} (a_{ij}x_j + b_{ij}x_j^2 + c_{ij}x_j^3) + \sum_{j=1}^{n} \sum_{k=j+1}^{n} d_{ijk}x_j x_k \cdots .$$

\* \* \* \* \*